US009340602B2

(12) United States Patent
Agrawal et al.

(10) Patent No.: US 9,340,602 B2
(45) Date of Patent: *May 17, 2016

(54) MATRICRYPTIC ECM PEPTIDES FOR TISSUE RECONSTRUCTION

(71) Applicant: University of Pittsburgh—Of the Commonwealth System of Higher Education, Pittsburgh, PA (US)

(72) Inventors: Vineet Agrawal, Pittsburgh, PA (US); Stephen F. Badylak, Pittsburgh, PA (US); Scott A. Johnson, Allison Park, PA (US); Stephen Tottey, Pittsburgh, PA (US)

(73) Assignee: University of Pittsburgh-Of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/248,465

(22) Filed: Apr. 9, 2014

(65) Prior Publication Data

US 2014/0294918 A1    Oct. 2, 2014

Related U.S. Application Data

(63) Continuation of application No. 13/500,398, filed as application No. PCT/US2010/051947 on Oct. 8, 2010, now Pat. No. 8,716,438.

(60) Provisional application No. 61/250,143, filed on Oct. 9, 2009.

(51) Int. Cl.

| A61K 38/08 | (2006.01) |
|---|---|
| A61K 38/10 | (2006.01) |
| A61K 38/04 | (2006.01) |
| C07K 7/06 | (2006.01) |
| C07K 7/08 | (2006.01) |
| C07K 7/00 | (2006.01) |
| A61P 17/02 | (2006.01) |
| A61K 38/00 | (2006.01) |
| C07K 14/78 | (2006.01) |
| A61K 35/22 | (2015.01) |

(52) U.S. Cl.
CPC .............. *C07K 14/78* (2013.01); *A61K 35/22* (2013.01); *A61K 38/00* (2013.01)

(58) Field of Classification Search
None
See application file for complete search history.

(56) References Cited

U.S. PATENT DOCUMENTS

| 4,693,718 A | 9/1987 | Urry et al. |
|---|---|---|
| 4,902,508 A | 2/1990 | Badylak et al. |
| 4,956,178 A | 9/1990 | Badylak et al. |
| 5,281,422 A | 1/1994 | Badylak et al. |
| 5,352,463 A | 10/1994 | Badylak et al. |
| 5,372,821 A | 12/1994 | Badylak et al. |
| 5,554,389 A | 9/1996 | Badylak et al. |
| 5,573,784 A | 11/1996 | Badylak et al. |
| 5,645,860 A | 7/1997 | Knapp, Jr. et al. |
| 5,753,267 A | 5/1998 | Badylak et al. |
| 5,762,966 A | 6/1998 | Knapp, Jr. et al. |
| 5,823,983 A | 10/1998 | Rosofsky et al. |
| 5,824,647 A | 10/1998 | Postlethwaite et al. |
| 5,866,414 A | 2/1999 | Badylak et al. |
| 6,069,864 A | 5/2000 | Kim |
| 6,096,864 A | 8/2000 | Broadley et al. |
| 6,099,567 A | 8/2000 | Badylak et al. |
| 6,485,723 B1 | 11/2002 | Badylak et al. |
| 6,576,265 B1 | 6/2003 | Spievack |
| 6,579,538 B1 | 6/2003 | Spievack |
| 6,696,270 B2 | 2/2004 | Badylak et al. |
| 6,783,776 B2 | 8/2004 | Spievack |
| 6,793,939 B2 | 9/2004 | Badylak |
| 6,849,273 B2 | 2/2005 | Spievack |
| 6,852,339 B2 | 2/2005 | Spievack |
| 6,861,074 B2 | 3/2005 | Spievack |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| 6,906,036 B2 | 6/2005 | Quirk et al. |
| 6,916,903 B2 * | 7/2005 | Eyre ................. C07K 14/78 530/300 |
| 2004/0191215 A1 | 9/2004 | Froix et al. |
| 2007/0014773 A1 | 1/2007 | Matheny et al. |
| 2012/0093740 A1 | 4/2012 | Harris et al. |

FOREIGN PATENT DOCUMENTS

WO    2008035843 A1    3/2008

OTHER PUBLICATIONS

Reing et al., Degradation Products of Extracellular Matrix Affect Cell Migration and Proliferation, Tissue Eng. Part A, vol. 15, No. 3, 2009, pp. 605-614.*
Adelman-Grill et al. Collagenolytic cleavage products of collage type I as chemoattractants for human dermal fibroblasts, J Soc. Biol., 1985, 104-107, 36(1).
Amatschek et al., Blood and lymphatic endothelial cell-specific differentiation programs are stringently controlled by the tissue environment, Blood, 2007, 4777-4785, 109(11).
Armour et al., A Comparison of Human and Porcine Acellularized Dermis: Interactions with Human Fibroblasts In Vitro, Plast. Reconstr. Surg., 2006, 845-856 117(3).
Badylak et al., Marrow-derived cells populate scaffolds composed of xenogeneic extracellular matrix, Experimental Hematology, 2001, 1310-1318, 29(11).

(Continued)

*Primary Examiner* — Karlheinz R Skowronek
*Assistant Examiner* — Joseph Fischer
(74) *Attorney, Agent, or Firm* — The Webb Law Firm

(57) ABSTRACT

Chemoattractant polypeptide compounds for progenitor cells and compositions and drug products comprising the compounds are provided herein. Methods for attracting progenitor cells to a location in or on a patient also are provided along with methods of growing and repairing bone.

15 Claims, 13 Drawing Sheets

(56) References Cited

OTHER PUBLICATIONS

Badylak et al., The use of xenogeneic small intestinal submucosa as a biomaterial for Achille's tendon repair in a dog model, Journal of Biomedical Materials Research, 1995, 977-985, 29(8).
Badylak et al., Small Intestinal Submucosa as a Large Diameter Vascular Graft in the Dog, Journal of Surgical Research, 1989, 74-80, 47(1).
Badylak et al., Esophageal Reconstruction with Ecm and Muscle Tissue in a Dog Model, Journal of Surgical Research, 2005, 87-97, 128(1).
Badylak S et al., Endothelial cell adherence to small intestinal submucosa: an acellular bioscaffold, Biomaterials, 1999, 2257-63, 20(23-24).
Beattie et al., Chemoattraction of Progenitor Cells by Remodeling Extracellular Matrix Scaffolds, Tissue Engineering: Part A, 2009, 1119-1125, vol. 15-5.
Bissell et al., Dynamic Reciprocity: How Do Extracellular Matrix and Hormones Direct Gene Expression?, Prog Clin Biol Res, 1987, 251-262, 249.
Brennan et al., Antibacterial Activity within Degradation Products of Biological Scaffolds Composed of Extracellular Matrix, Tissue Eng., Oct. 2006, 2949-2955, 12(10).
Brennan et al., Chemoattractant activity of degradation products of fetal and adult skin extracellular matrix for keratinocyte progenitor cells, J Tissue Eng Regen Med, Dec. 2008 491-498, 2(8).
Brown et al., The Basement Membrane Component of Biologic Scaffolds Derived from Extracellular Matrix, Tissue Engineering, 2006, 519-526, 12(3).
Cebotari et al., Clinical Application of Tissue Engineered Human Heart Valves Using Autologous Progenitor Cells, Circulation, 2006, I-132-I-137 114.
Charge et al., Cellular and Molecular Regulation of Muscle Regeneration, Physiol Rev., 2004, 209-238, 84(1).
Chen et al., Acellular Collagen Matrix as a Possible "Off the Shelf" Biomaterial for Urethral Repair, Urology, 1999, 407-410, 54(3).
Clark et al., A New Murine Model for Mammalian Wound Repair and Regeneration, Clinical Immunology and Immunopathology, 1998, 35-45, 88(1).
Crisan et al., A Perivascular Origin for Mesenchymal Stem Cells in Multiple Human Organs, Cell Stem Cell, 2008, 301-313, 3(3).
Ewalt et al., Is Lamina Propria Matrix Responsible for Normal Bladder Compliance? The Journal of Urology, 1992, 544-549, 148.
Freytes et al., Biaxial strength of multilaminated extracellular matrix scaffolds, Biomaterials, 2004, 2325-2361, 25(12).
Freytes et al., Effect of Storage Upon Material Properties of Lyophilized Porcine Extracellular Matrix Derived from the Urinary Bladder, J Biomed Mater Res Part B: Appl Biomater, 2006, 327-333, 78B.
Gennaro, Ed. Remington: The Science and Practice of Pharmacy, 20th Edition, 2000.
Gerbino, PP, Remington: The Science and Practice of Pharmacy, 2006, 21st Edition, Lippincott Williams & Wilkins, Philadelphia.
Gilbert et al., Production and characterization of ECM powder: implications for tissue engineering applications, Biomaterials, 2005, 1431-1435, 26(12).
Heber-Katz et al., Spallanzani's Mouse: A Model of Restoration and Regeneration, Curr Top Microbiol Immunol, 2003, 165-189, 280.
Holtom et al., Porcine Small Intestine Submucosa Does Not Show Antimicrobial Properties, Clinical Orthopaedics and Related Research, 2004, 18-21, 427.

Huber et al., Extracellular Matrix as a Scaffold for Laryngeal Reconstruction, Ann Otol Rhinol Laryngol, 2003, 428-433, 112(5).
Kropp et al., Experimental Assessment of Small Intestinal Submucosa as a Bladder Wall Substitute, Urology, 1995, 396-400, 46(3).
Kun et al., Effect of vasoactive peptides on adhesion and chemotaxis elicited by extracellular matrix protein sequences, FEBS Journal, 2005, 272, 272(s1).
Le Roux, Endoscopic Urethroplasty With Unseeded Small Intestinal Submucosa Collagen Matrix Grafts: A Pilot Study, The Journal of Urololgy, 2005, 140-143, 173(1).
Li et al., Low-Molecular-Weight Peptides Derived from Extracellular Matrix as Chemoattractants for Primary Endothelial Cells, Endothelium, 2004, 199-206, 11(3-4).
Lichtenberg et al., Preclinical Testing of Tissue-Engineered Heart Valves Re-Endothelialized Under Simulated Physiological Conditions, Circulation, 2006, I-559-I-565, 114(1 Suppl).
Mantovani et al., Reconstructive Urethroplasty Using Porcine Acellular Matrix, Eurropean Urology, 2003, 600-602, 44(5).
Postlethwaite et al., Chemotactic attraction of human fibroblasts to type I, II, and III collagens and collagen-derived peptides, Proc. Natl. Acad. Sci. USA, 1978, 871-875, 1978; 75(2).
Reing et al., Degradation Products of Extracellular Matrix Affect Cell Migration and Proliferation, Tissue Engineering: Part A, 2009, 605-614, 15(3).
Rosso et al., From Cell-ECM Interactions to Tissue Engineering, Journal of Cellular Physiology, 2004, 174-180, 199.
Sacks et al., Quantification of the fiber architecture and biaxial mechanical behavior of porcine intestinal submucosa, J Biomed Mater Res, 1999, 1-10, 46.
Samulewicz et al., Expression of preadipocyte factor-1, a delta-like protein, in healing mouse ears, Wound Repair Regen, 2002, 215-221, 10.
Sarikaya et al., Antimicrobial Activity Associated with Extracellular Matrices, Tissue Engineering, 2002, 63-71, 8(1).
Sclamberg et al., Six-month magnetic resonance imaging follow-up of large and massive rotator cuff repairs reinforced with porcine small intestinal submucosa, Journal of Shoulder Elbow Surgery, 2004, 538-541, 13(5).
Thibault et al., Fibronectin, Vitronectin, and Collagen I Induce Chemotaxis and Haptotaxis of Human and Rabbit Mesenchymal Stem Cells in a Standardized Transmembrane Assay, Stem Cells and Development, 2007, 489-502, 16(3).
Valentin et al., Extracellular Matrix Bioscaffolds for Orthopaedic Applications: A Comparative Histologic Study, The Journal of Bone and Joint Surgery, Incorporated, 2006, 2673-2686, Am 88(12).
van Amerongen et al., The enzymatic degradation of scaffolds and their replacement by vascularized extracellular matrix in the murine myocardium, Biomaterials, 2006, 2247-2257, 27(10).
Voytik-Harbin et al., Identification of Extractable Growth Factors From Small Intestinal Submucosa, Journal of Cellular Biochemistry, 1997, 478-491, 67.
Walles et al., Influence of scaffold thickness and scaffold composition on bioartificial graft survival, Biomaterials, 2003, 1233-1239, 24(7).
Zantop et al., Extracellular Matrix Scaffolds are Repopulated by Bone Marrow-Derived Cells in a Mouse Model of Achilles Tendon Reconstruction, Journal of Orthopaedic Research, 2006, 1299-1309, 24(6).

* cited by examiner

| | | |
|---|---|---|
| Peptide 1 | IAGVGGEKSGGF | (SEQ ID NO: 1) |
| Rat | IAGVGGEKSGGF | (SEQ ID NO: 1) |
| Rabbit | IAGVGGEKSGGF | (SEQ ID NO: 1) |
| Mouse | IAGVGGEKSGGF | (SEQ ID NO: 1) |
| Human | IAGIGGEKAGGF | (SEQ ID NO: 4) |
| Chimpanzee | IAGIGGEKAGGF | (SEQ ID NO: 4) |
| Orangutan | IAGIGGEKAGGY | (SEQ ID NO: 5) |
| Bovine | IAGVGAEKAGGF | (SEQ ID NO: 6) |

*Fig. 1A*

| | | |
|---|---|---|
| Peptide 2 | GPVGPSGPPGK | (SEQ ID NO: 2) |
| Rat | GPVGPHGPPGK | (SEQ ID NO: 7) |
| Rabbit | GPVGPSGPPGK | (SEQ ID NO: 2) |
| Mouse | GPVGPHGPPGK | (SEQ ID NO: 7) |
| Human | GPVGPSGPPGK | (SEQ ID NO: 2) |
| Chimpanzee | GPVGPSGPPGK | (SEQ ID NO: 2) |
| Orangutan | GPVGPSGPPGK | (SEQ ID NO: 2) |
| Bovine | GPVGPSGPPGK | (SEQ ID NO: 2) |

*Fig. 1B*

PIG     (DBEST ID: 2465055, GENBANK NO. AU058685.1)

GSEGSPGHPGQPGPPGPPGAPGPCCGGGAAAIAGVGGEKSGGFAPYYGDEPMDFKINTDEIM

TSLKSVNGQIESLISPDG     (SEQ ID NO: 8)

RAT         (GENE ID: 84032 COL3A1, GENBANK NO. NP_114474.1)

PGPVGPSGKNGDRGETGPAGPSGAPGPAGARGAPGPQGPRGDKGETGERGSNGIKGHRGFPGNPGPPGSP

GAAGHQGAVGSPGPAGPRGPVGPHGPPGKDGSSGHPGPIGPPGPRGNRGERGSEGSPGHPGQPGPPGPPG

APGPCCGGGAAIAGVGGEKSGGFSPYYGDDPMDFKINTEEIMSSLKSVNGQIESLISPDGSRKNPARNCR

DLKFCHPELKSGEYWVDPNQGCKMDAIKVFCNMETGETCINASPMTVPRKHWWTDAGAEKKHVWFGESMN (SEQ ID NO: 9)

RABBIT     (GENE ID: 100009177, GENBANK NO. XP_002712379.1)

PGVNGQNGERGPPGPQGLPGLAGTAGEPGRDGNPGSDGQPGRDGAPGGKGDRGENGSPGAPGAPGHPGPP

GPVGPAGKSGDRGETGPAGPSGAPGPAGARGAPGPQGPRGDKGETGERGANGIKGHRGFPGNPGPPGSPG

PSGHQGAVGSPGPAGPRGPVGPSGPPGKDGTSGHPGPIGPPGPRGNRGERGSEGSPGHPGQPGPPGPPGA

PGPCCGGAAAIAGVGGEKSGGFAPYYGDDPMDFKTNTEEIMSSLKSVNGQIESLISPDGSRKNPARNCRD

LKFCHPELKSGEYWVDPNQGCKLDAIKVFCNMETGETCVNANPLSIPRKKWWTDSGAEKKHVWFGESMDG (SEQ ID NO: 10)

ORANGUTAN     (GENE ID: 100457897, GENBANK NO. XP_002812713.1)

VAGPPGGSGPAGPPGPQGVKGERGSPGGPGPAGPAGAPGPAGSRGAPGPQGPRGDKGETGERGATGIKGH

RGFPGNPGAPGSPGPAGQQGAIGSPGPAGPRGPVGPSGPPGKDGTSGHPGPIGPPGPRGNRGERGSEGSP

GHPGQPGPPGPPGAPGPCCGGVGAAAIAGIGGEKAGGYAPYYGDEPMDFKINTDEIMTSLKSVNGQIESL

ISPDGSRKNPARNCRDLKFCHPELKSGEYWVDPNQGCKLDAIKVFCNMETGETCISASPLNVPRKHWWTD (SEQ ID NO: 11)

BOVINE     (GENE ID: 510833 COL3A1, GENBANK NO. DAA32863.1)

GKPGPSGQNGERGPPGPQGLPGLAGTAGEPGRDGNPGSDGLPGRDGAPGAKGDRGENGSPGAPGAPGHPG

PPGPVGPAGKSGDRGETGPAGPSGAPGPAGSRGPPGPQGPRGDKGETGERGAMGIKGHRGFPGNPGAPGS

PGPAGHQGAVGSPGPAGPRGPVGPSGPPGKDGASGHPGPIGPPGPRGNRGERGSEGSPGHPGQPGPPGPP

GAPGPCCGAGGVAAIAGVGAEKAGGFAPYYGDEPIDFKINTDEIMTSLKSVNGQIESLISPDGSRKNPAR

NCRDLKFCHPELQSGEYWVDPNQGCKLDAIKVYCNMETGETCISASPLTIPQKNWWTDSGAEKKHVWFGE (SEQ ID NO: 12)

*Fig. 1C-1*

MOUSE      (GENE ID: 12825 COL3A1, GENBANK NO. AAH28248.1)
GNPGSDGQPGRDGSPGGKGDRGENGSPGAPGAPGHPGPPGPVGPSGKSGDRGETGPAGPSGAPGPAGARG
APGPQGPRGDKGETGERGSNGIKGHRGFPGNPGPPGSPGAAGHQGAIGSPGPAGPRGPVGPHGPPGKDGT
SGHPGPIGPPGPRGNRGERGSEGSPGHPGQPGPPGPPGAPGPCCGGGAAAIAGVGGEKSGGFSPYYGDDP
MDFKINTEEIMSSLKSVNGQIESLISPDGSRKNPARNCRDLKFCHPELKSGEYWVDPNQGCKMDAIKVFC
NMETGETCINASPMTVPRKHWWTDSGAEKKHVWFGESMNGGFQFSYGTPDLPEDVVDVQLAFLRLLSSRA
(SEQ ID NO: 13)

CHIMPANZEE (GENE ID: 459815 COL3A1, GENBANK NO. XP_001163292.1)
GKPGANGLSGERGPPGPQGLPGLAGTAGEPGRDGNPGSDGLPGRDGSPGGKGDRGENGSPGAPGAPGHPG
PPGPVGPAGKSGDRGESGPAGPAGAPGPAGSRGAPGPQGPRGDKGETGERGAAGIKGHRGFPGNPGAPGS
PGPAGQQGAIGSPGPAGPRGPVGPSGPPGKDGTSGHPGPIGPPGPRGNRGERGSEGSPGHPGQPGPPGPP
GAPGPCCGGVGAAAIAGIGGEKAGGFAPYYGDEPMDFKINTDEIMTSLKSVNGQIESLISPDGSRKNPAR
NCRDLKFCHPELKSGEYWVDPNQGCKLDAIKVFCNMETGETCISANPLNVPRKHWWTDSSAEKKHVWFGE
(SEQ ID NO: 14)

*Fig. 1C-2*

HUMAN      (GENE ID: 1281 COL3A1, GENBANK NO. CAA29886.1)
AGITGARGLAGPPGMPGPRGSPGPQGVKGESGKPGANGLSGERGPPGPQGLPGLAGTAGEPGRDGNPGSY
GLPGRDGSPGGKGDRGENGSPGAPGAPGHPGPPGPVGPAGKSGDRGESGPAGPAGAPGPAGSRGAPGPQG
PRGDKGETGERGAAGIKGHRGFPGNPGAPGSPGPAGQQGAIGSPGPAGPRGPVGPSGPPGKDGTSGHPGP
IGPPGPRGNRGERGSEGSPGHPGQPGPPGPPGAPGPCCGGVGAAAIAGIGGEKAGGFAPYYGDEPMDFKI
NTDEIMTSLKSANGQIESLISPDGSRKNPARNCRDLKFCHPELKSGEYWVDPNQGCKLDAIKVFCNMETG
ETCISANPLNVPRKHWWTDSSAEKKHVWFGESMDGGFQFSYGNPELPEDVLDVQLAFLRLLSSRASQNIT
YHCKNSIAYMDQASGNVKKALKLMGSNEGEFKAEGNSKFTYTVLEDGCTKHTGEWSKTVFEYRTRKAVRL
PIVDIAPYDIGGPDQEFGVDVGPVCFL   (SEQ ID NO: 15)

*Fig. 1D*

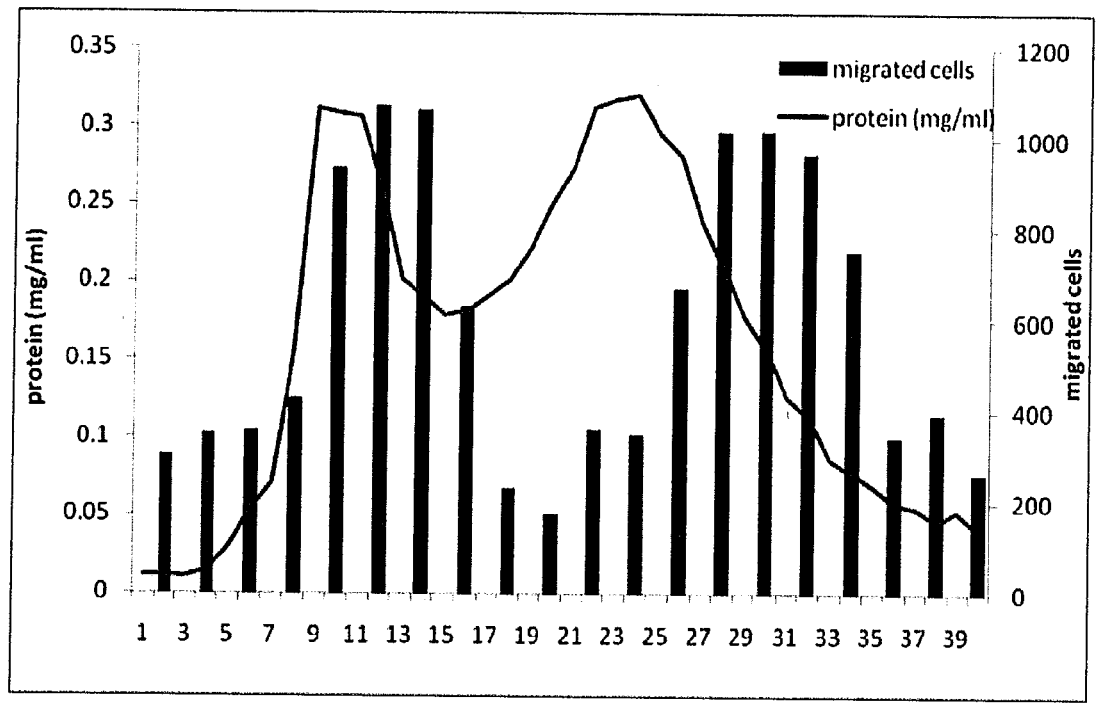
*Fig. 8*
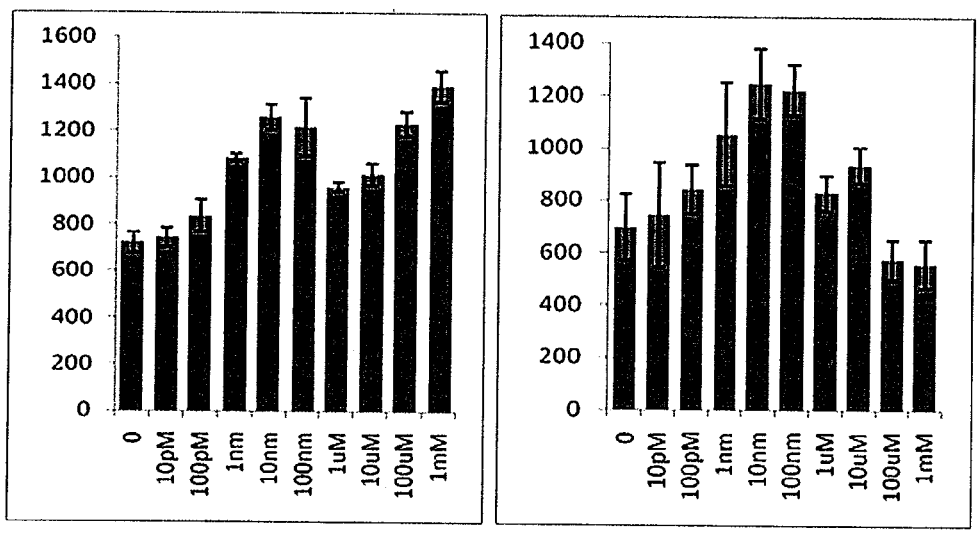
*Fig. 9*          *Fig. 10*

 
Fig. 11G                    Fig. 11H
 
Fig. 12A                    Fig. 12B

SEQUENCE LISTING

```
<160> NUMBER OF SEQ ID NOS: 43

<210> SEQ ID NO 1
<211> LENGTH: 12
<212> TYPE: PRT
<213> ORGANISM: Sus scrofa

<400> SEQUENCE: 1

Ile Ala Gly Val Gly Gly Glu Lys Ser Gly Gly Phe
1               5                   10

<210> SEQ ID NO 2
<211> LENGTH: 11
<212> TYPE: PRT
<213> ORGANISM: Sus scrofa

<400> SEQUENCE: 2

Gly Pro Val Gly Pro Ser Gly Pro Pro Gly Lys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Conserved Peptide 1 generic sequence.
<220> FEATURE:
<221> NAME/KEY: R1
<222> LOCATION: (4)..(4)
<223> OTHER INFORMATION: Ile or Val
<220> FEATURE:
<221> NAME/KEY: R2
<222> LOCATION: (6)..(6)
<223> OTHER INFORMATION: Gly or Ala
```

```
<220> FEATURE:
<221> NAME/KEY: R3
<222> LOCATION: (9)..(9)
<223> OTHER INFORMATION: Ser or Ala
<220> FEATURE:
<221> NAME/KEY: R4
<222> LOCATION: (12)..(12)
<223> OTHER INFORMATION: Phe or Tyr

<400> SEQUENCE: 3

Ile Ala Gly Xaa Gly Xaa Glu Lys Xaa Gly Gly Xaa
1               5                   10

<210> SEQ ID NO 4
<211> LENGTH: 12
<212> TYPE: PRT
<213> ORGANISM: Homo sapiens

<400> SEQUENCE: 4

Ile Ala Gly Ile Gly Gly Glu Lys Ala Gly Gly Phe
1               5                   10

<210> SEQ ID NO 5
<211> LENGTH: 12
<212> TYPE: PRT
<213> ORGANISM: Pongo abelii

<400> SEQUENCE: 5

Ile Ala Gly Ile Gly Gly Glu Lys Ala Gly Gly Tyr
1               5                   10

<210> SEQ ID NO 6
<211> LENGTH: 12
<212> TYPE: PRT
<213> ORGANISM: Bos taurus

<400> SEQUENCE: 6

Ile Ala Gly Val Gly Ala Glu Lys Ala Gly Gly Phe
1               5                   10

<210> SEQ ID NO 7
<211> LENGTH: 11
<212> TYPE: PRT
<213> ORGANISM: Rattus norvegicus

<400> SEQUENCE: 7

Gly Pro Val Gly Pro His Gly Pro Pro Gly Lys
1               5                   10

<210> SEQ ID NO 8
<211> LENGTH: 80
<212> TYPE: PRT
<213> ORGANISM: Sus scrofa

<400> SEQUENCE: 8

Gly Ser Glu Gly Ser Pro Gly His Pro Gly Gln Pro Gly Pro Pro Gly
1               5                   10                  15

Pro Pro Gly Ala Pro Gly Pro Cys Cys Gly Gly Ala Ala Ala Ile
            20                  25                  30

Ala Gly Val Gly Gly Glu Lys Ser Gly Gly Phe Ala Pro Tyr Tyr Gly
        35                  40                  45
```

```
Asp Glu Pro Met Asp Phe Lys Ile Asn Thr Asp Glu Ile Met Thr Ser
            50                  55                  60

Leu Lys Ser Val Asn Gly Gln Ile Glu Ser Leu Ile Ser Pro Asp Gly
65                  70                  75                  80

<210> SEQ ID NO 9
<211> LENGTH: 280
<212> TYPE: PRT
<213> ORGANISM: Rattus norvegicus

<400> SEQUENCE: 9

Pro Gly Pro Val Gly Pro Ser Gly Lys Asn Gly Asp Arg Gly Glu Thr
1               5                   10                  15

Gly Pro Ala Gly Pro Ser Gly Ala Pro Gly Pro Ala Gly Ala Arg Gly
            20                  25                  30

Ala Pro Gly Pro Gln Gly Pro Arg Gly Asp Lys Gly Glu Thr Gly Glu
        35                  40                  45

Arg Gly Ser Asn Gly Ile Lys Gly His Arg Gly Phe Pro Gly Asn Pro
    50                  55                  60

Gly Pro Pro Gly Ser Pro Gly Ala Ala Gly His Gln Gly Ala Val Gly
65                  70                  75                  80

Ser Pro Gly Pro Ala Gly Pro Arg Gly Pro Val Gly Pro His Gly Pro
                85                  90                  95

Pro Gly Lys Asp Gly Ser Ser Gly His Pro Gly Pro Ile Gly Pro Pro
            100                 105                 110

Gly Pro Arg Gly Asn Arg Gly Glu Arg Gly Ser Glu Gly Ser Pro Gly
        115                 120                 125

His Pro Gly Gln Pro Gly Pro Pro Gly Pro Pro Gly Ala Pro Gly Pro
    130                 135                 140

Cys Cys Gly Gly Ala Ala Ile Ala Gly Val Gly Gly Glu Lys Ser
145                 150                 155                 160

Gly Gly Phe Ser Pro Tyr Tyr Gly Asp Asp Pro Met Asp Phe Lys Ile
                165                 170                 175

Asn Thr Glu Glu Ile Met Ser Ser Leu Lys Ser Val Asn Gly Gln Ile
            180                 185                 190

Glu Ser Leu Ile Ser Pro Asp Gly Ser Arg Lys Asn Pro Ala Arg Asn
        195                 200                 205

Cys Arg Asp Leu Lys Phe Cys His Pro Glu Leu Lys Ser Gly Glu Tyr
    210                 215                 220

Trp Val Asp Pro Asn Gln Gly Cys Lys Met Asp Ala Ile Lys Val Phe
225                 230                 235                 240

Cys Asn Met Glu Thr Gly Glu Thr Cys Ile Asn Ala Ser Pro Met Thr
                245                 250                 255

Val Pro Arg Lys His Trp Trp Thr Asp Ala Gly Ala Glu Lys Lys His
            260                 265                 270

Val Trp Phe Gly Glu Ser Met Asn
        275                 280

<210> SEQ ID NO 10
<211> LENGTH: 350
<212> TYPE: PRT
<213> ORGANISM: Oryctolagus cuniculus
```

-continued

<400> SEQUENCE: 10

Pro Gly Val Asn Gly Gln Asn Gly Glu Arg Gly Pro Pro Gly Pro Gln
1               5                   10                  15

Gly Leu Pro Gly Leu Ala Gly Thr Ala Gly Glu Pro Gly Arg Asp Gly
            20                  25                  30

Asn Pro Gly Ser Asp Gly Gln Pro Gly Arg Asp Gly Ala Pro Gly Gly
        35                  40                  45

Lys Gly Asp Arg Gly Glu Asn Gly Ser Pro Gly Ala Pro Gly Ala Pro
50                  55                  60

Gly His Pro Gly Pro Gly Pro Val Gly Pro Ala Gly Lys Ser Gly
65                  70                  75                  80

Asp Arg Gly Glu Thr Gly Pro Ala Gly Pro Ser Gly Ala Pro Gly Pro
                85                  90                  95

Ala Gly Ala Arg Gly Ala Pro Gly Pro Gln Gly Pro Arg Gly Asp Lys
            100                 105                 110

Gly Glu Thr Gly Glu Arg Gly Ala Asn Gly Ile Lys Gly His Arg Gly
        115                 120                 125

Phe Pro Gly Asn Pro Gly Pro Gly Ser Pro Gly Pro Ser Gly His
130                 135                 140

Gln Gly Ala Val Gly Ser Pro Gly Pro Ala Gly Pro Arg Gly Pro Val
145                 150                 155                 160

Gly Pro Ser Gly Pro Pro Gly Lys Asp Gly Thr Ser Gly His Pro Gly
                165                 170                 175

Pro Ile Gly Pro Pro Gly Pro Arg Gly Asn Arg Gly Glu Arg Gly Ser
            180                 185                 190

Glu Gly Ser Pro Gly His Pro Gly Gln Pro Gly Pro Pro Gly Pro Pro
        195                 200                 205

Gly Ala Pro Gly Pro Cys Cys Gly Gly Ala Ala Ile Ala Gly Val
210                 215                 220

Gly Gly Glu Lys Ser Gly Gly Phe Ala Pro Tyr Tyr Gly Asp Asp Pro
225                 230                 235                 240

Met Asp Phe Lys Thr Asn Thr Glu Glu Ile Met Ser Ser Leu Lys Ser
                245                 250                 255

Val Asn Gly Gln Ile Glu Ser Leu Ile Ser Pro Asp Gly Ser Arg Lys
            260                 265                 270

Asn Pro Ala Arg Asn Cys Arg Asp Leu Lys Phe Cys His Pro Glu Leu
        275                 280                 285

Lys Ser Gly Glu Tyr Trp Val Asp Pro Asn Gln Gly Cys Lys Leu Asp
290                 295                 300

Ala Ile Lys Val Phe Cys Asn Met Glu Thr Gly Glu Thr Cys Val Asn
305                 310                 315                 320

Ala Asn Pro Leu Ser Ile Pro Arg Lys Lys Trp Trp Thr Asp Ser Gly
                325                 330                 335

Ala Glu Lys Lys His Val Trp Phe Gly Glu Ser Met Asp Gly
            340                 345                 350

<210> SEQ ID NO 11
<211> LENGTH: 280
<212> TYPE: PRT
<213> ORGANISM: Pongo abelii

<400> SEQUENCE: 11

```
Val Ala Gly Pro Pro Gly Ser Gly Pro Ala Gly Pro Pro Gly Pro
1               5                   10                  15

Gln Gly Val Lys Gly Glu Arg Gly Ser Pro Gly Gly Pro Gly Pro Ala
            20                  25                  30

Gly Pro Ala Gly Ala Pro Gly Pro Ala Gly Ser Arg Gly Ala Pro Gly
        35                  40                  45

Pro Gln Gly Pro Arg Gly Asp Lys Gly Glu Thr Gly Glu Arg Gly Ala
    50                  55                  60

Thr Gly Ile Lys Gly His Arg Gly Phe Pro Gly Asn Pro Gly Ala Pro
65                  70                  75                  80

Gly Ser Pro Gly Pro Ala Gly Gln Gln Gly Ala Ile Gly Ser Pro Gly
            85                  90                  95

Pro Ala Gly Pro Arg Gly Pro Val Gly Ser Gly Pro Pro Gly Lys
        100                 105                 110

Asp Gly Thr Ser Gly His Pro Gly Pro Ile Gly Pro Pro Gly Pro Arg
    115                 120                 125

Gly Asn Arg Gly Glu Arg Gly Ser Glu Gly Ser Pro Gly His Pro Gly
130                 135                 140

Gln Pro Gly Pro Pro Gly Pro Pro Gly Ala Pro Gly Pro Cys Cys Gly
145                 150                 155                 160

Gly Val Gly Ala Ala Ala Ile Ala Gly Ile Gly Gly Glu Lys Ala Gly
            165                 170                 175

Gly Tyr Ala Pro Tyr Tyr Gly Asp Glu Pro Met Asp Phe Lys Ile Asn
        180                 185                 190

Thr Asp Glu Ile Met Thr Ser Leu Lys Ser Val Asn Gly Gln Ile Glu
    195                 200                 205

Ser Leu Ile Ser Pro Asp Gly Ser Arg Lys Asn Pro Ala Arg Asn Cys
210                 215                 220

Arg Asp Leu Lys Phe Cys His Pro Glu Leu Lys Ser Gly Glu Tyr Trp
225                 230                 235                 240

Val Asp Pro Asn Gln Gly Cys Lys Leu Asp Ala Ile Lys Val Phe Cys
            245                 250                 255

Asn Met Glu Thr Gly Glu Thr Cys Ile Ser Ala Ser Pro Leu Asn Val
        260                 265                 270

Pro Arg Lys His Trp Trp Thr Asp
    275                 280

<210> SEQ ID NO 12
<211> LENGTH: 350
<212> TYPE: PRT
<213> ORGANISM: Bos taurus

<400> SEQUENCE: 12

Gly Lys Pro Gly Pro Ser Gly Gln Asn Gly Glu Arg Gly Pro Pro Gly
1               5                   10                  15

Pro Gln Gly Leu Pro Gly Leu Ala Gly Thr Ala Gly Glu Pro Gly Arg
            20                  25                  30

Asp Gly Asn Pro Gly Ser Asp Gly Leu Pro Gly Arg Asp Gly Ala Pro
        35                  40                  45

Gly Ala Lys Gly Asp Arg Gly Glu Asn Gly Ser Pro Gly Ala Pro Gly
    50                  55                  60

Ala Pro Gly His Pro Gly Pro Pro Gly Pro Val Gly Pro Ala Gly Lys
65                  70                  75                  80
```

```
Ser Gly Asp Arg Gly Glu Thr Gly Pro Ala Gly Pro Ser Gly Ala Pro
            85                  90                  95

Gly Pro Ala Gly Ser Arg Gly Pro Pro Gly Pro Gln Gly Pro Arg Gly
        100                 105                 110

Asp Lys Gly Glu Thr Gly Glu Arg Gly Ala Met Gly Ile Lys Gly His
    115                 120                 125

Arg Gly Phe Pro Gly Asn Pro Gly Ala Pro Gly Ser Pro Gly Pro Ala
130                 135                 140

Gly His Gln Gly Ala Val Gly Ser Pro Gly Pro Ala Gly Pro Arg Gly
145                 150                 155                 160

Pro Val Gly Pro Ser Gly Pro Pro Gly Lys Asp Gly Ala Ser Gly His
                165                 170                 175

Pro Gly Pro Ile Gly Pro Pro Gly Pro Arg Gly Asn Arg Gly Glu Arg
            180                 185                 190

Gly Ser Glu Gly Ser Pro Gly His Pro Gly Gln Pro Gly Pro Pro Gly
        195                 200                 205

Pro Pro Gly Ala Pro Gly Pro Cys Cys Gly Ala Gly Gly Val Ala Ala
    210                 215                 220

Ile Ala Gly Val Gly Ala Glu Lys Ala Gly Phe Ala Pro Tyr Tyr
225                 230                 235                 240

Gly Asp Glu Pro Ile Asp Phe Lys Ile Asn Thr Asp Glu Ile Met Thr
                245                 250                 255

Ser Leu Lys Ser Val Asn Gly Gln Ile Glu Ser Leu Ile Ser Pro Asp
            260                 265                 270

Gly Ser Arg Lys Asn Pro Ala Arg Asn Cys Arg Asp Leu Lys Phe Cys
        275                 280                 285

His Pro Glu Leu Gln Ser Gly Glu Tyr Trp Val Asp Pro Asn Gln Gly
    290                 295                 300

Cys Lys Leu Asp Ala Ile Lys Val Tyr Cys Asn Met Glu Thr Gly Glu
305                 310                 315                 320

Thr Cys Ile Ser Ala Ser Pro Leu Thr Ile Pro Gln Lys Asn Trp Trp
                325                 330                 335

Thr Asp Ser Gly Ala Glu Lys Lys His Val Trp Phe Gly Glu
            340                 345                 350

<210> SEQ ID NO 13
<211> LENGTH: 350
<212> TYPE: PRT
<213> ORGANISM: Mus musculus

<400> SEQUENCE: 13

Gly Asn Pro Gly Ser Asp Gly Gln Pro Gly Arg Asp Gly Ser Pro Gly
1               5                   10                  15

Gly Lys Gly Asp Arg Gly Glu Asn Gly Ser Pro Gly Ala Pro Gly Ala
            20                  25                  30

Pro Gly His Pro Gly Pro Pro Gly Pro Val Gly Pro Ser Gly Lys Ser
        35                  40                  45

Gly Asp Arg Gly Glu Thr Gly Pro Ala Gly Pro Ser Gly Ala Pro Gly
    50                  55                  60

Pro Ala Gly Ala Arg Gly Ala Pro Gly Pro Gln Gly Pro Arg Gly Asp
65                  70                  75                  80

Lys Gly Glu Thr Gly Glu Arg Gly Ser Asn Gly Ile Lys Gly His Arg
                85                  90                  95

Gly Phe Pro Gly Asn Pro Gly Pro Pro Gly Ser Pro Gly Ala Ala Gly
            100                 105                 110
```

-continued

```
His Gln Gly Ala Ile Gly Ser Pro Gly Pro Ala Gly Pro Arg Gly Pro
        115                 120                 125

Val Gly Pro His Gly Pro Pro Gly Lys Asp Gly Thr Ser Gly His Pro
130                 135                 140

Gly Pro Ile Gly Pro Pro Gly Pro Arg Gly Asn Arg Gly Glu Arg Gly
145                 150                 155                 160

Ser Glu Gly Ser Pro Gly His Pro Gly Gln Pro Gly Pro Pro Gly Pro
                165                 170                 175

Pro Gly Ala Pro Gly Pro Cys Cys Gly Gly Ala Ala Ile Ala
            180                 185                 190

Gly Val Gly Glu Lys Ser Gly Gly Phe Ser Pro Tyr Tyr Gly Asp
        195                 200                 205

Asp Pro Met Asp Phe Lys Ile Asn Thr Glu Glu Ile Met Ser Ser Leu
    210                 215                 220

Lys Ser Val Asn Gly Gln Ile Glu Ser Leu Ile Ser Pro Asp Gly Ser
225                 230                 235                 240

Arg Lys Asn Pro Ala Arg Asn Cys Arg Asp Leu Lys Phe Cys His Pro
                245                 250                 255

Glu Leu Lys Ser Gly Glu Tyr Trp Val Asp Pro Asn Gln Gly Cys Lys
            260                 265                 270

Met Asp Ala Ile Lys Val Phe Cys Asn Met Glu Thr Gly Glu Thr Cys
        275                 280                 285

Ile Asn Ala Ser Pro Met Thr Val Pro Arg Lys His Trp Trp Thr Asp
    290                 295                 300

Ser Gly Ala Glu Lys Lys His Val Trp Phe Gly Glu Ser Met Asn Gly
305                 310                 315                 320

Gly Phe Gln Phe Ser Tyr Gly Thr Pro Asp Leu Pro Glu Asp Val Val
                325                 330                 335

Asp Val Gln Leu Ala Phe Leu Arg Leu Leu Ser Ser Arg Ala
            340                 345                 350

<210> SEQ ID NO 14
<211> LENGTH: 350
<212> TYPE: PRT
<213> ORGANISM: Pan troglodytes

<400> SEQUENCE: 14

Gly Lys Pro Gly Ala Asn Gly Leu Ser Gly Glu Arg Gly Pro Pro Gly
1               5                   10                  15

Pro Gln Gly Leu Pro Gly Leu Ala Gly Thr Ala Gly Glu Pro Gly Arg
            20                  25                  30

Asp Gly Asn Pro Gly Ser Asp Gly Leu Pro Gly Arg Asp Gly Ser Pro
        35                  40                  45

Gly Gly Lys Gly Asp Arg Gly Glu Asn Gly Ser Pro Gly Ala Pro Gly
    50                  55                  60

Ala Pro Gly His Pro Gly Pro Pro Gly Pro Val Gly Pro Ala Gly Lys
65                  70                  75                  80

Ser Gly Asp Arg Gly Glu Ser Gly Pro Ala Gly Pro Ala Gly Ala Pro
                85                  90                  95

Gly Pro Ala Gly Ser Arg Gly Ala Pro Gly Pro Gln Gly Pro Arg Gly
            100                 105                 110

Asp Lys Gly Glu Thr Gly Glu Arg Gly Ala Ala Gly Ile Lys Gly His
        115                 120                 125

Arg Gly Phe Pro Gly Asn Pro Gly Ala Pro Gly Ser Pro Gly Pro Ala
    130                 135                 140
```

```
Gly Gln Gln Gly Ala Ile Gly Ser Pro Gly Ala Gly Pro Arg Gly
145                 150                 155                 160

Pro Val Gly Pro Ser Gly Pro Pro Gly Lys Asp Gly Thr Ser Gly His
            165                 170                 175

Pro Gly Pro Ile Gly Pro Pro Gly Pro Arg Gly Asn Arg Gly Glu Arg
            180                 185                 190

Gly Ser Glu Gly Ser Pro Gly His Pro Gly Gln Pro Gly Pro Pro Gly
        195                 200                 205

Pro Pro Gly Ala Pro Gly Pro Cys Cys Gly Gly Val Gly Ala Ala Ala
    210                 215                 220

Ile Ala Gly Ile Gly Gly Glu Lys Ala Gly Phe Ala Pro Tyr Tyr
225                 230                 235                 240

Gly Asp Glu Pro Met Asp Phe Lys Ile Asn Thr Asp Glu Ile Met Thr
            245                 250                 255

Ser Leu Lys Ser Val Asn Gly Gln Ile Glu Ser Leu Ile Ser Pro Asp
        260                 265                 270

Gly Ser Arg Lys Asn Pro Ala Arg Asn Cys Arg Asp Leu Lys Phe Cys
    275                 280                 285

His Pro Glu Leu Lys Ser Gly Glu Tyr Trp Val Asp Pro Asn Gln Gly
290                 295                 300

Cys Lys Leu Asp Ala Ile Lys Val Phe Cys Asn Met Glu Thr Gly Glu
305                 310                 315                 320

Thr Cys Ile Ser Ala Asn Pro Leu Asn Val Pro Arg Lys His Trp Trp
            325                 330                 335

Thr Asp Ser Ser Ala Glu Lys Lys His Val Trp Phe Gly Glu
        340                 345                 350

<210> SEQ ID NO 15
<211> LENGTH: 517
<212> TYPE: PRT
<213> ORGANISM: Homo sapiens

<400> SEQUENCE: 15

Ala Gly Ile Thr Gly Ala Arg Gly Leu Ala Gly Pro Pro Gly Met Pro
1               5                   10                  15

Gly Pro Arg Gly Ser Pro Gly Pro Gln Gly Val Lys Gly Glu Ser Gly
            20                  25                  30

Lys Pro Gly Ala Asn Gly Leu Ser Gly Glu Arg Gly Pro Pro Gly Pro
        35                  40                  45

Gln Gly Leu Pro Gly Leu Ala Gly Thr Ala Gly Glu Pro Gly Arg Asp
    50                  55                  60

Gly Asn Pro Gly Ser Tyr Gly Leu Pro Gly Arg Asp Gly Ser Pro Gly
65                  70                  75                  80

Gly Lys Gly Asp Arg Gly Glu Asn Gly Ser Pro Gly Ala Pro Gly Ala
                85                  90                  95

Pro Gly His Pro Gly Pro Pro Gly Pro Val Gly Pro Ala Gly Lys Ser
            100                 105                 110

Gly Asp Arg Gly Glu Ser Gly Pro Ala Gly Pro Ala Gly Ala Pro Gly
        115                 120                 125

Pro Ala Gly Ser Arg Gly Ala Pro Gly Pro Gln Gly Pro Arg Gly Asp
    130                 135                 140

Lys Gly Glu Thr Gly Glu Arg Gly Ala Ala Gly Ile Lys Gly His Arg
145                 150                 155                 160

Gly Phe Pro Gly Asn Pro Gly Ala Pro Gly Ser Pro Gly Pro Ala Gly
                165                 170                 175
```

-continued

```
Gln Gln Gly Ala Ile Gly Ser Pro Gly Pro Ala Gly Pro Arg Gly Pro
            180                 185                 190

Val Gly Pro Ser Gly Pro Pro Gly Lys Asp Gly Thr Ser Gly His Pro
        195                 200                 205

Gly Pro Ile Gly Pro Pro Gly Pro Arg Gly Asn Arg Gly Glu Arg Gly
    210                 215                 220

Ser Glu Gly Ser Pro Gly His Pro Gly Gln Pro Gly Pro Pro Gly Pro
225                 230                 235                 240

Pro Gly Ala Pro Gly Pro Cys Cys Gly Val Gly Ala Ala Ala Ile
                245                 250                 255

Ala Gly Ile Gly Gly Glu Lys Ala Gly Gly Phe Ala Pro Tyr Tyr Gly
            260                 265                 270

Asp Glu Pro Met Asp Phe Lys Ile Asn Thr Asp Glu Ile Met Thr Ser
        275                 280                 285

Leu Lys Ser Ala Asn Gly Gln Ile Glu Ser Leu Ile Ser Pro Asp Gly
    290                 295                 300

Ser Arg Lys Asn Pro Ala Arg Asn Cys Arg Asp Leu Lys Phe Cys His
305                 310                 315                 320

Pro Glu Leu Lys Ser Gly Glu Tyr Trp Val Asp Pro Asn Gln Gly Cys
                325                 330                 335

Lys Leu Asp Ala Ile Lys Val Phe Cys Asn Met Glu Thr Gly Glu Thr
            340                 345                 350

Cys Ile Ser Ala Asn Pro Leu Asn Val Pro Arg Lys His Trp Trp Thr
        355                 360                 365

Asp Ser Ser Ala Glu Lys Lys His Val Trp Phe Gly Glu Ser Met Asp
    370                 375                 380

Gly Gly Phe Gln Phe Ser Tyr Gly Asn Pro Glu Leu Pro Glu Asp Val
385                 390                 395                 400

Leu Asp Val Gln Leu Ala Phe Leu Arg Leu Leu Ser Ser Arg Ala Ser
                405                 410                 415

Gln Asn Ile Thr Tyr His Cys Lys Asn Ser Ile Ala Tyr Met Asp Gln
            420                 425                 430

Ala Ser Gly Asn Val Lys Lys Ala Leu Lys Leu Met Gly Ser Asn Glu
        435                 440                 445

Gly Glu Phe Lys Ala Glu Gly Asn Ser Lys Phe Thr Tyr Thr Val Leu
    450                 455                 460

Glu Asp Gly Cys Thr Lys His Thr Gly Glu Trp Ser Lys Thr Val Phe
465                 470                 475                 480

Glu Tyr Arg Thr Arg Lys Ala Val Arg Leu Pro Ile Val Asp Ile Ala
                485                 490                 495

Pro Tyr Asp Ile Gly Gly Pro Asp Gln Glu Phe Gly Val Asp Val Gly
            500                 505                 510

Pro Val Cys Phe Leu
        515

<210> SEQ ID NO 16
<211> LENGTH: 29
<212> TYPE: DNA
<213> ORGANISM: Mus musculus

<400> SEQUENCE: 16
cggatccgtt tggagaccgc acagaagaa                                     29
```

```
<210> SEQ ID NO 17
<211> LENGTH: 30
<212> TYPE: DNA
<213> ORGANISM: Mus musculus

<400> SEQUENCE: 17
cgcaagcttt gtccccatat ctgcccatca                                    30

<210> SEQ ID NO 18
<211> LENGTH: 21
<212> TYPE: DNA
<213> ORGANISM: Mus musculus

<400> SEQUENCE: 18
caaggtcctt accctagcca a                                             21

<210> SEQ ID NO 19
<211> LENGTH: 23
<212> TYPE: DNA
<213> ORGANISM: Mus musculus

<400> SEQUENCE: 19
ccagcttgtc tctatacaca ctg                                           23

<210> SEQ ID NO 20
<211> LENGTH: 24
<212> TYPE: DNA
<213> ORGANISM: Mus musculus

<400> SEQUENCE: 20
acaatgtctg caggtgccat gttg                                          24

<210> SEQ ID NO 21
<211> LENGTH: 24
<212> TYPE: DNA
<213> ORGANISM: Mus musculus

<400> SEQUENCE: 21
aggagcattc gtactggcct ttct                                          24

<210> SEQ ID NO 22
<211> LENGTH: 20
<212> TYPE: DNA
<213> ORGANISM: Mus musculus

<400> SEQUENCE: 22
ctctcggcca tttctcagtc                                               20

<210> SEQ ID NO 23
<211> LENGTH: 20
<212> TYPE: DNA
<213> ORGANISM: Mus musculus

<400> SEQUENCE: 23
tactgcttct ggcggaactt                                               20

<210> SEQ ID NO 24
<211> LENGTH: 24
<212> TYPE: DNA
<213> ORGANISM: Mus musculus

<400> SEQUENCE: 24
atcgcgaagc tgctatccag ttct                                          24
```

```
<210> SEQ ID NO 25
<211> LENGTH: 24
<212> TYPE: DNA
<213> ORGANISM: Mus musculus

<400> SEQUENCE: 25
tcttcatctg cctcaaggaa gcca                                          24

<210> SEQ ID NO 26
<211> LENGTH: 24
<212> TYPE: DNA
<213> ORGANISM: Mus musculus

<400> SEQUENCE: 26
atattgttcc cgcagacgac caca                                          24

<210> SEQ ID NO 27
<211> LENGTH: 24
<212> TYPE: DNA
<213> ORGANISM: Mus musculus

<400> SEQUENCE: 27
taatgtgtcc aaacgggtcc aggt                                          24

<210> SEQ ID NO 28
<211> LENGTH: 22
<212> TYPE: DNA
<213> ORGANISM: Mus musculus

<400> SEQUENCE: 28
cgcaacgacc ccttcattga cc                                            22

<210> SEQ ID NO 29
<211> LENGTH: 22
<212> TYPE: DNA
<213> ORGANISM: Mus musculus

<400> SEQUENCE: 29
cgatgagccc ttccacaatg cc                                            22

<210> SEQ ID NO 30
<211> LENGTH: 24
<212> TYPE: DNA
<213> ORGANISM: Homo sapiens

<400> SEQUENCE: 30
agatgtcaca gacaccactg cctt                                          24

<210> SEQ ID NO 31
<211> LENGTH: 24
<212> TYPE: DNA
<213> ORGANISM: Homo sapiens

<400> SEQUENCE: 31
tgtggcttgt tggctctttg gaac                                          24

<210> SEQ ID NO 32
<211> LENGTH: 24
<212> TYPE: DNA
<213> ORGANISM: Homo sapiens

<400> SEQUENCE: 32
cccgaaccaa cttcaccagc aaat                                          24
```

```
<210> SEQ ID NO 33
<211> LENGTH: 24
<212> TYPE: DNA
<213> ORGANISM: Homo sapiens

<400> SEQUENCE: 33
tctctgcact ggaacttgag gctt                                              24

<210> SEQ ID NO 34
<211> LENGTH: 23
<212> TYPE: DNA
<213> ORGANISM: Homo sapiens

<400> SEQUENCE: 34
ctggacgatg gcctctatga atg                                               23

<210> SEQ ID NO 35
<211> LENGTH: 20
<212> TYPE: DNA
<213> ORGANISM: Homo sapiens

<400> SEQUENCE: 35
atcatccacg caggtgcctc                                                   20

<210> SEQ ID NO 36
<211> LENGTH: 20
<212> TYPE: DNA
<213> ORGANISM: Homo sapiens

<400> SEQUENCE: 36
tcctcaagct gccagaagat                                                   20

<210> SEQ ID NO 37
<211> LENGTH: 20
<212> TYPE: DNA
<213> ORGANISM: Homo sapiens

<400> SEQUENCE: 37
acggttcgtc ttgtgtttgc                                                   20

<210> SEQ ID NO 38
<211> LENGTH: 24
<212> TYPE: DNA
<213> ORGANISM: Homo sapiens

<400> SEQUENCE: 38
tgacaaggac aactgcagac tcgt                                              24

<210> SEQ ID NO 39
<211> LENGTH: 24
<212> TYPE: DNA
<213> ORGANISM: Homo sapiens

<400> SEQUENCE: 39
aggaatcatc tggaatcggc ggaa                                              24

<210> SEQ ID NO 40
<211> LENGTH: 24
<212> TYPE: DNA
<213> ORGANISM: Homo sapiens

<400> SEQUENCE: 40
acattgtacc tgccgacgat caca                                              24
```

```
<210> SEQ ID NO 41
<211> LENGTH: 24
<212> TYPE: DNA
<213> ORGANISM: Homo sapiens

<400> SEQUENCE: 41
agacgtgagt gcagaacggc ttat                                          24

<210> SEQ ID NO 42
<211> LENGTH: 19
<212> TYPE: DNA
<213> ORGANISM: Homo sapiens

<400> SEQUENCE: 42
gaaggtgaag gtcggagtc                                                19

<210> SEQ ID NO 43
<211> LENGTH: 20
<212> TYPE: DNA
<213> ORGANISM: Homo sapiens

<400> SEQUENCE: 43
gaagatggtg atgggatttc                                               20
```

MATRICRYPTIC ECM PEPTIDES FOR TISSUE RECONSTRUCTION

CROSS REFERENCE TO RELATED APPLICATIONS

This application is a continuation of co-pending U.S. patent application Ser. No. 13/500,398, filed Nov. 5, 2012, issued as U.S. Pat. No. 8,716,438, which was the National Stage of International Patent Application No. PCT/US2010/051947, filed Oct. 8, 2010, which claims the benefit under 35 U.S.C. §119(e) to U.S. Provisional Patent Application No. 61/250,143, filed Oct. 9, 2009, each of which is incorporated herein by reference in its entirety.

The Sequence Listing associated with this application is filed in electronic format via EFS-Web and is hereby incorporated by reference into the specification in its entirety. The name of the text file containing the Sequence Listing is 143215_ST25.txt. The size of the text file is 28,450 bytes, and the text file was created on Apr. 8, 2014.

Biologic scaffolds composed of extracellular matrix (ECM) are utilized in numerous regenerative medicine applications to facilitate the constructive remodeling of tissues and organs. The mechanisms by which the host remodeling response occurs are not fully understood, but recent studies suggest that both constituent growth factors and biologically active degradation products derived from ECM play important roles.

The extracellular matrix (ECM) represents the secreted product of resident cells within every tissue and organ and thus defines a preferred collection of structural and functional molecules best suited to support the viability and phenotype of those cells. The ECM is in a state of dynamic reciprocity with the cells of each tissue, and the growth factors, cytokines, chemokines, and other signaling molecules within the ECM play important roles in development, homeostasis, and response to injury. A variety of mammalian tissues and organs, including the small intestine, liver, urinary bladder, arterial vasculature, heart valves, and dermis, have been decellularized, and the remaining ECM used as a biologic scaffold to support the reconstruction of injured or missing tissues. The mechanisms by which these biologic scaffolds facilitate tissue remodeling include both contact guidance and molecular signaling, but the temporal and spatial patterns of these events remain largely unknown.

Previous studies have shown that nonphysiologic methods of ECM degradation such as acid and heat can produce low molecular weight molecules that have angiogenic (Li, F., et al. Low-molecular-weight peptides derived from extracellular matrix as chemoattractants for primary endothelial cells. *Endothelium* 11(3-4), 199, 2004), chemoattractant (Li, F., et al. *Endothelium* 11(3-4), 199, 2004; Badylak, S. F., et al. Marrow-derived cells populate scaffolds composed of xenogeneic extracellular matrix. *Exp Hematol* 29(11), 1310, 2001; and Zantop, T., et al. Extracellular matrix scaffolds attract bone marrow derived cells in a mouse model of Achilles tendon reconstruction. *J Orthop Res* 24(6), 1299, 2006), and antimicrobial (Brennan, E. P., et al. Antibacterial activity within degradation products of biological scaffolds composed of extracellular matrix. *Tissue Eng* 12(10), 2949, 2006 and Sarikaya, A., et al. Antimicrobial activity associated with extracellular matrices. *Tissue Eng* 8(1), 63, 2002) properties. Interestingly, degradation of the ECM scaffold is necessary to realize these biologic effects. It has been clearly shown that intact ECM has no antimicrobial effects, while degradation products of the same ECM are able to strongly inhibit bacterial growth (Brennan, E. P., et al. *Tissue Eng* 12(10), 2949, 2006; Sarikaya, A., et al. *Tissue Eng* 8(1), 63, 2002); and Holtom, P. D., et al. Porcine small intestine submucosa does not show antimicrobial properties. *Clin Orthop Relat Res* 427, 18, 2004). Similarly, if ECM scaffolds are chemically crosslinked such that they are resistant to degradation, the host remodeling response is markedly altered toward fibrous encapsulation and chronic inflammation rather than constructive remodeling (Valentin, J. E., Badylak, J. S., McCabe, G. P., and Badylak, S. F. Extracellular matrix bioscaffolds for orthopaedic applications: a comparative histologic study. *J Bone Joint Surg Am* 88(12), 2673, 2006). It is clear that the products and biologic effects of ECM degradation are different from the components of the intact ECM.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. 1 5R01 AR053603 03, awarded by the National Institutes of Health.

SUMMARY

Described herein is the identification of bioactive molecules derived from the biologically digested extracellular matrix of porcine urinary bladder (UBM). Implantation of solid UBM has been shown to promote tissue regeneration and constructive remodeling. In part this is believed to be caused by the degradation in the patient of the UBM construct, releasing peptides that promote an increase in the presence of progenitor cells at the site of implantation. In vitro or in vivo digestion of UBM tissue releases peptides which cause the movement of mulitpotent progenitor cells towards the peptides. By using a combination of liquid chromatography, biological assays and mass spectrometry the peptides responsible for progenitor cell recruitment can be identified. It is expected that the placement of synthesized versions these peptides at the site of damage (i.e., injury) will cause the recruitment of a patient's own progenitor cells to the injury and promote tissue healing. This invention would allow for the relocation of patient specific mulitpotent progenitor cells to the site of need without the practical and ethical problems of harvesting and implanting stem cells.

BRIEF DESCRIPTION OF THE DRAWINGS

FIG. 1A shows and alignment of sequences identified in a BLAST search of Peptide 1.

FIG. 1B shows and alignment of sequences identified in a BLAST search of Peptide 2.

FIG. 1C Provides partial amino acid sequences for Type III Collagen, alpha 1 ("ColIIIA1") in pig, rat, rabbit, orangutan, cow, mouse and chimpanzee (SEQ ID NOS: 8, 9, 10, 11, 12, 13 and 14, respectively). FIG. 1D provides the complete amino acid sequence for human ColIIIA1 (SEQ ID NO: 15). Sequences corresponding to Peptides 1 and 2 are identified in bold and are underlined. Native flanking sequences are shown for all depicted sequences.

FIG. 8 is a graph showing that fractionated matricryptic ECM peptides contain chemotactic capacity. This confirms the chemotactic activity for progenitor cells within ECM degradation products. Human perivascular stem cells were assessed in vitro in a Boyden chamber.

FIGS. 9 and 10 confirm the chemotactic activity for progenitor cells within ECM degradation products, human perivascular stem cells were assessed in vitro in a Boyden chamber. FIGS. 9 and 10 show these results for Peptides 1 and 2, respectively.

FIGS. 11A-11H are photomicrographs showing in vivo bone formation. Amputated digits treated with either (FIGS. 11A, B, E and F) Peptide 1 or (FIGS. 11C, D, G and H) buffer and tissue harvested after 14 days. Sections were stained with H&E (FIGS. 11A-D) or trichrome (FIGS. 11E-H). Arrow indicates bone nodule formation. Images taken at 4× (left) or 10× (right).

FIGS. 12A and 12B are photomicrographs showing addition of the isolated peptide changes the wound healing response. Amputated digits were treated with (FIG. 12A) buffer or (FIG. 12B) peptide and tissue harvested after 14 days and stained with Alcian blue.

DETAILED DESCRIPTION

Figure 2:
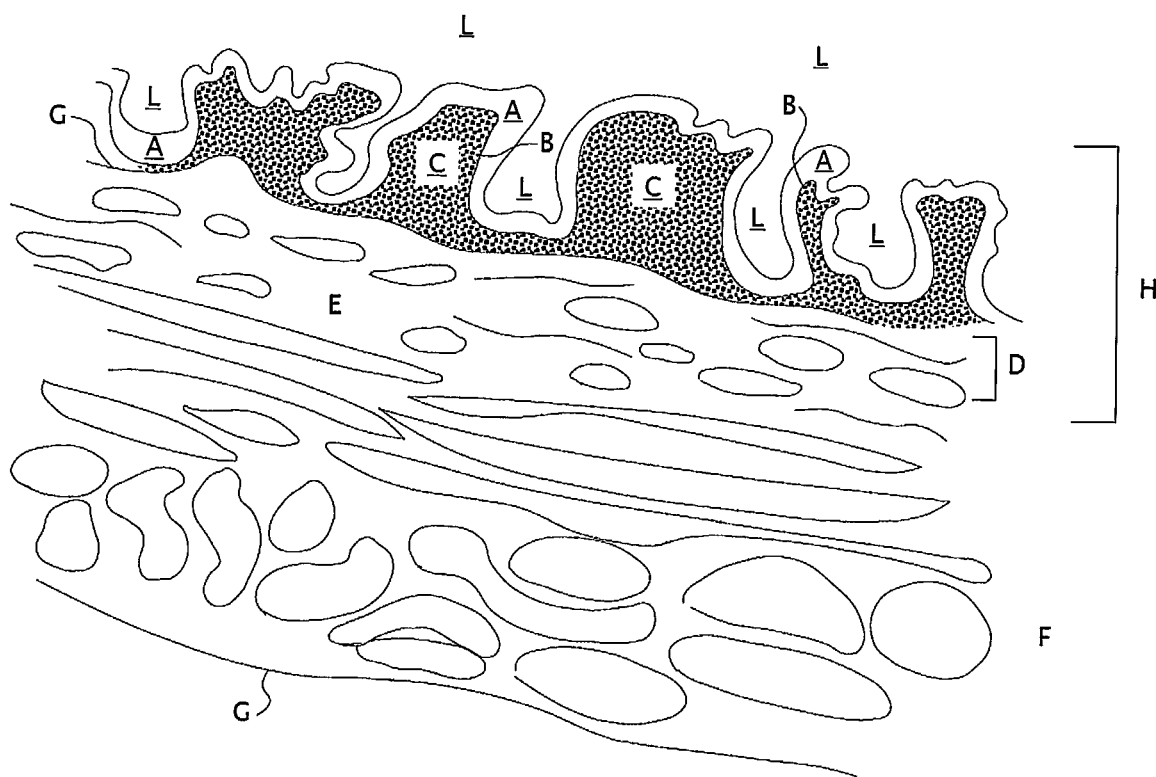
FIG. 2 shows schematically a cross-sectional view of the wall of the urinary bladder (not drawn to scale). The following structures are shown: epithelial cell layer (A), basement membrane (B), tunica propria (C), muscularis mucosa (D), tunica mucosa (E), tunica muscularis externa (F), tunica serosa (G), tunica mucosa (H), and lumen of the bladder (L).

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

A progenitor cell is a cell that can differentiate under certain conditions into a more-differentiated cell type. Non-limiting examples of progenitor cells include stem cells that may be totipotent, pluripotent, multipotent stem cells, or referred to as progenitor cells. Additional non-limiting examples of progenitor cells include perivascular stem cells, blastema cells, and multilineage progenitor cells.

As used herein, the "treatment" or "treating" of a wound or defect means administration to a patient by any suitable dosage regimen and administration route of a composition with the object of achieving a desirable clinical/medical end-point, including attracting progenitor cells, healing a wound, correcting a defect, etc. As used herein, the term "patient" refers to members of the animal kingdom including but not limited to mammals and human beings and is not limited to humans or animals in a doctor-patient or veterinarian-patient relationship.

Provided herein are compounds useful in attracting progenitor cells to a location in (in, on, into, onto, etc.) a patient, for example in wound healing and/or tissue regeneration. Blastema like structures can be formed as a result of administration of the compounds at a location (site, wound, position, etc.) in a patient. By the phrase "attracting progenitor cells," and like phrases, it is meant that the compounds have the effect of attracting (e.g., chemoattracting) progenitor cells to a location, which may include, but which does not necessarily include, proliferation and/or differentiation of the progenitor cells at the location, and formation of a blastema or a like structure also referred to herein as a multipotential cell cluster (MCC). A number of relevant end-points may be used to determine the effectiveness of a compound in "attracting a progenitor cell to a location in a patient," including in vitro assays described herein and in vivo end-points, such as increases of progenitor cells at a location of administration of the compound, formation of structures, such as blastema, blastema-like structures, an MCC, etc.

In one embodiment, the compound is an isolated and purified polypeptide having the sequence IAGVGGEKSGGF (SEQ ID NO: 1, "Peptide 1"), or a pharmaceutically acceptable salt thereof. In another embodiment, the compound is an isolated and purified polypeptide having the sequence GPVGPSGPPGK (SEQ ID NO: 2, "Peptide 2"), or a pharmaceutically acceptable salt thereof. Included within the definition of "isolated and purified" are both synthetic peptide preparations, recombinant peptide preparations (such as by preparing a suitable genetic construct for production of the polypeptide, for example by one or more of many methods well-known in the art) and a fraction of peptides obtained from tissue in which the polypeptide is substantially purified. Recombinant methods for peptide preparation are well-known in the field of molecular biology, and suitable vectors, plasmid constructs, etc. are commercially available. In one embodiment, the polypeptides are produced by recombinant methods to include a suitable tag, such as a His (e.g., 6×His), Strep, or GST tag, and purified using commercially-available technologies in mammalian, bacterial, yeast or insect cells or in vitro. A large variety of suitable cloning vectors, including vectors for producing tagged proteins are available from Invitrogen of Carlsbad, Calif. Affinity purification systems for tagged proteins also are available from Qiagen, of Germantown, Md.

A sequence alignment was performed in which Peptide 1 was aligned with sequences of the same protein (native analogs) in species other than pig. As shown in FIG. 1A, the sequence is strongly conserved in mammalian Collagen, type III, alpha 1 ("ColIII1A") protein, yielding a consensus sequence of IAG-$R_1$-GR$_2$-EK-R$_3$-GG-R$_4$ where $R_1$ is Ile or Val; $R_2$ is Gly or Ala, $R_3$ is Ser or Ala and $R_4$ is Phe or Tyr (SEQ ID NO: 3). In many instances, $R_2$ is Gly and $R_4$ is Phe. In one non-limiting embodiment, when $R_2$ is Ala, $R_1$ is Val. Analogs described herein may be native analogs, meaning they are portions of sequences found in nature, or synthetic analogs, meaning they are not sequences found in nature. As shown in FIG. 1B, a sequence alignment also was performed in which Peptide 2 was aligned with sequences of the same protein (native analogs) in species other than pig, with the sequence being highly (greater than 90%) conserved in many mammalian species, including humans, mice, primates, and cow, Yielding the variants: GPVGPSGPPGK (SEQ ID NO: 2) and GPVGPHGPPGK (SEQ ID NO: 7).

It should be noted that the isolated and purified polypeptides were initially obtained by pepsin digestion of porcine ECM material. Pepsin primarily attacks aromatic amino acid residues, such as phenylalanine, tryptophan and tyrosine. However, papain digestion (a cysteine protease) also yielded similar activity. As such, polypeptide fragments comprising amino acid sequences comprising either a portion or all of the 12 contiguous amino acids of Peptide 1 or the a portion or all of the 11 contiguous amino acids of Peptide 2, plus, optionally one or more native flanking amino acids are expected to have similar activity. Also, due to the inter-species degeneracy of the amino acid sequence of Peptide 1, cross-species efficacy of both polypeptides as shown in the Examples below, and that the natively-generated fragments will likely have additional amino acids, an isolated and purified polypeptide, such as an oligopeptide (a polypeptide of between 2 and 20 amino acids), consisting essentially of the sequences of Peptide 1 or Peptide 2, or analogs thereof, for instance with at least 75% identity with Peptide 1 is expected to exhibit the same activity as Peptides 1 and 2. By percent identity, it is meant that a sequence is aligned with a reference sequence (e.g., Peptide 1 or 2) and 75% or more of the amino acids align with and are identical to the reference sequence. In reference to Peptide 1, as shown in FIG. 1, the rat, rabbit and mouse sequences have 100% identity, the monkey sequence has 92% identity (11/12), the human, chimpanzee and bovine sequences have 83% identity (10/12) and the orangutan sequence have 75% identity (9/12).

By "consisting essentially of" it is meant that a polypeptide comprises the stated sequences plus any additional amino acid residues that do not substantially negatively impact the chemoattractive function of the stated polypeptide. Polypeptides consisting essentially of the stated sequences do not include full-length collagen proteins and typically are 11-100, and more typically 11-50, amino acids in length, including all increments therebetween including polypeptides of 11, 12, 13, 14, 15, 16, 17, 18, 19, 20, 21 22, 23, 24, 25, 26, 27, 28, 29, 50, and other integers within that range, and in many instances the polypeptides are preferably oligopeptides, which are no more than 20 amino acids in length.

In one embodiment sequences flanking the stated polypeptide are sequences that flank a corresponding wild-type amino acid sequence from the same or a different species (e.g., that flank Peptide 1, Peptide 2 or a native analog thereof shown in FIGS. 1A and 1B). FIG. 1C provides partial amino acid sequences for ColIIIA1 in pig, rat, rabbit, orangutan, cow, mouse and chimpanzee (SEQ ID NOS: 8, 9, 10, 11, 12, 13 and 14, respectively) and FIG. 1D provides the complete amino acid sequence for human ColIIIA1 (SEQ ID NO: 15). Sequences corresponding to Peptides 1 and 2, as shown in FIGS. 1A and 1B, are identified in bold and are underlined. Native flanking sequences are shown for all depicted sequences and given the teachings herein, intra-species or inter-species allelic variations in these flanking sequences are readily identifiable. These flanking sequences are referred to herein as "contiguous native ColIIIA1 flanking amino acids" and include but are not limited to contiguous flanking amino acids immediately adjacent to (attached to) the bold and underlined sequences shown in FIGS. 1C and 1D. The flanking native amino acids are described as contiguous, meaning that they include consecutive amino acids found in a wild-type amino acid sequence immediately adjacent to a described sequence or a native analog thereof. As a non-limiting example, and for clarity, a polypeptide may consist of the sequence IAGVGGEKSGGF (SEQ ID NO: 1, also residues 32-43 of SEQ ID NO: 8 which depicts 31 N-terminal flanking amino acids and 37 C-terminal flanking amino acids), and including at its N-terminal end from 1-31 additional contiguous flanking amino acids, such as residue 31, residues 30-31, residues 29-31, etc. of SEQ ID NO: 8 (contiguous residues from any one of residues 1 to 31 to residue 31 of SEQ ID NO: 8) and/or including at its C-terminal end from 1-37 additional contiguous flanking amino acids such as residue 44, residues 44-45, residues 44-46, etc. of SEQ ID NO: 8 (contiguous residues from residue 44 to any one of residues 44-80 of SEQ ID NO: 8) and thus, in other words, consisting of from 12-80 consecutive amino acids of SEQ ID NO: 8 raging from any one of residues 1-32 of SEQ ID NO: 8 at its N-terminus to any one of residues 44-80 of SEQ ID NO: 8 at its C-terminus. As an additional example, a polypeptide "consisting essentially of Peptide 1" includes polypeptides consisting of Peptide 1, may, in one embodiment comprise on one or both of its N-terminal or C-terminal ends from 1-50 contiguous native ColIIIA1 flanking amino acids depicted in one or more of SEQ ID NOS: 8-15. The native flanking sequences do not necessarily have to come from the protein of the same species as the stated polypeptide, such that Peptide 1 (porcine) may be flanked on its N- or C-terminus with 0, 1, 2, 3, 4, 5, 6, 7, 8, 9, 10, etc. consecutive flanking amino acids from one or more of SEQ ID NOS: 9-15.

"Isolated and purified polypeptides" consisting essentially of the stated sequences exclude specifically any natively-generated polypeptide mixtures (peptide mixtures produced by in vivo degradation of ECM), or digests of ECM that are not substantially enriched or essentially completely enriched for the specified polypeptide(s). Nevertheless, the isolated and purified polypeptide can be separated from all or substantially all other polypeptide fragments produced from a protein digest by using separation methods, such as affinity chromatography, or other suitable methods, such as the methods described in the Examples below, and would be considered isolated and purified.

Therefore, polypeptide(s) useful for the purposes described herein:

1) consist of or consist essentially of sequence IAG-$R_1$-GR$_2$-EK-$R_3$-GG-$R_4$, where $R_1$ is Ile or Val; $R_2$ is Gly or Ala, $R_3$ is Ser or Ala and $R_4$ is Phe or Tyr (SEQ ID NO: 3), e.g., IAGVGGEKSGGF (SEQ ID NO: 1); the sequence GPVGPSGPPGK (SEQ ID NO: 2); or the sequence GPVGPHGPPGK (SEQ ID NO: 7), or a pharmaceutically acceptable salt of thereof;

2) consist of or consist essentially of a sequence having 75% or greater identity with IAGVGGEKSGGF (SEQ ID NO: 1); a sequence having greater than 90% identity with GPVGPSGPPGK (SEQ ID NO: 2), or a pharmaceutically acceptable salt of thereof;

3) consist of or consist essentially one of the sequences IAGVGGEKSGGF (SEQ ID NO: 1) or GPVGPSGP-PGK (SEQ ID NO: 2), or a pharmaceutically acceptable salt thereof; or 4) consist of 12-50 amino acids comprising: the sequence IAG-$R_1$-GR$_2$-EK-$R_3$-GG-$R_4$, where $R_1$ is Ile or Val; $R_2$ is Gly or Ala, $R_3$ is Ser or Ala and $R_4$ is Phe or Tyr (SEQ ID NO: 3); a sequence having 75% or greater identity with IAGVGGEKSGGF (SEQ ID NO: 1); a sequence having greater than 90% identity with GPVGPSGPPGK (SEQ ID NO: 2); the sequence IAGVGGEKSGGF (SEQ ID NO: 1); the sequence GPVGPSGPPGK (SEQ ID NO: 2); or the sequence GPVGPHGPPGK (SEQ ID NO: 7), or a pharmaceutically acceptable salt thereof.

In one embodiment, the polypeptide is not (SEQ ID NO: 8). Collectively, these polypeptides may be referred to as "Peptide 1, Peptide 2 and analogs thereof."

Pharmaceutically acceptable organic and inorganic salt forms of any of the compounds or compositions described herein may be prepared by conventional methods known in the pharmaceutical arts. For example and without limitation, where the compound comprises a carboxylic acid group, a suitable salt thereof may be formed by reacting the compound with an appropriate base to provide the corresponding base addition salt. Non-limiting examples include: alkali metal hydroxides, such as potassium hydroxide, sodium hydroxide and lithium hydroxide; alkaline earth metal hydroxides, such as barium hydroxide and calcium hydroxide; alkali metal alkoxides, such as potassium ethanolate and sodium propanolate; and various organic bases such as piperidine, diethanolamine, and N-methylglutamine. Acid addition salts may be prepared by treating a compound with pharmaceutically acceptable organic and inorganic acids, including, without limitation: hydrohalides, such as hydrochloride, hydrobromide, hydroiodide; other mineral acids and their corresponding salts such as sulfates, nitrates, and phosphates; alkyl- and mono-arylsulfonates, such as ethanesulfonate, toluenesulfonate, and benzenesulfonate; and other organic acids and their corresponding salts, such as acetate, tartrate, maleate, succinate, citrate, benzoate, salicylate, and ascorbate.

Non-limiting examples of pharmaceutically-acceptable base salts include: aluminum, ammonium, calcium, copper, ferric, ferrous, lithium, magnesium, manganic, manganous, potassium, sodium, and zinc salts. Salts derived from pharmaceutically acceptable organic non-toxic bases include, without limitation: salts of primary, secondary, and tertiary amines, substituted amines including naturally occurring substituted amines, cyclic amines, and basic ion exchange resins, such as arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine, and tris-(hydroxymethyl)-methylamine (tromethamine).

Non-limiting examples of pharmaceutically-acceptable acid salts include: acetate, adipate, alginate, arginate, aspartate, benzoate, besylate (benzenesulfonate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate, galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate, and phthalate.

Multiple salts forms are also considered to be pharmaceutically-acceptable salts. Common, non-limiting examples of multiple salt forms include: bitartrate, diacetate, difumarate, dimeglumine, diphosphate, disodium, and trihydrochloride.

For example and without limitation, a composition comprising an amount of the polypeptide effective to attract a progenitor cell to a location in a patient, may comprise a concentration of at least about 100 pM (picomolar) Peptide 1 and/or Peptide 2, or any polypeptide described above, or pharmaceutically acceptable salts thereof, including any and all increments, with a maximum concentration in the dosage form limited only by toxicity and/or solubility of the polypeptide, or salt thereof in a given dosage form. Thus, the concentration of a given polypeptide in a drug product may range from 10 pM to 1M (molar) or higher, including 100 pM, 250 pM, 500 pM, 1 nM (nanomolar), 10 nM, 100 nM, 250 nM, 500 nM, 1 μM (micromolar), 10 μM, 100 μM, 250 μM, 500 μM, 1 mM (millimolar), 10 mM, 100 mM, 250 mM, 500 mM, 1M, 2M, etc.

The compounds typically are administered in an amount and dosage regimen to attract progenitor cells to a location in a patient. The compounds may be administered in any manner that is effective for that purpose. Examples of delivery routes include, without limitation: topical, for example, epicutaneous, inhalational, enema, ocular, otic and intranasal delivery; parenteral, for example, intramuscular, intracardiac, subcutaneous, intraosseous, intradermal, intrathecal, transdermal, iontophoretic, transmucosal, epidural and intravitreal, with localized delivery to a specific location or site in a patient, such as topical (including administration to a wound and/or surrounding areas), and transdermal approaches, being preferred in many instances, and systemic delivery being disfavored in many instances.

The compounds may be compounded or otherwise manufactured into a suitable composition for use, such as in a drug product in which the compound is an active ingredient. The composition or drug product comprises one or more isolated and purified polypeptides that:

1) consist of or consist essentially of sequence IAG-$R_1$-$GR_2$-EK-$R_3$-GG-$R_4$, where $R_1$ is Ile or Val; $R_2$ is Gly or Ala, $R_3$ is Ser or Ala and $R_4$ is Phe or Tyr (SEQ ID NO: 3), e.g., IAGVGGEKSGGF (SEQ ID NO: 1); the sequence GPVGPSGPPGK (SEQ ID NO: 2); or the sequence GPVGPHGPPGK (SEQ ID NO: 7), or a pharmaceutically acceptable salt of thereof;

2) consist of or consist essentially of a sequence having 75% or greater identity with IAGVGGEKSGGF (SEQ ID NO: 1); a sequence having greater than 90% identity with GPVGPSGPPGK (SEQ ID NO: 2), or a pharmaceutically acceptable salt of thereof;

3) consist of or consist essentially one of the sequences IAGVGGEKSGGF (SEQ ID NO: 1) or GPVGPSGPPGK (SEQ ID NO: 2), or a pharmaceutically acceptable salt thereof; or 4) consist of 12-50 amino acids comprising: the sequence IAG-$R_1$-$GR_2$-EK-$R_3$-GG-$R_4$, where $R_1$ is Ile or Val; $R_2$ is Gly or Ala, $R_3$ is Ser or Ala and $R_4$ is Phe or Tyr (SEQ ID NO: 3); a sequence having 75% or greater identity with IAGVGGEKSGGF (SEQ ID NO: 1); a sequence having greater than 90% identity with GPVGPSGPPGK (SEQ ID NO: 2); the sequence IAGVGGEKSGGF (SEQ ID NO: 1); the sequence GPVGPSGPPGK (SEQ ID NO: 2); or the sequence GPVGPHGPPGK (SEQ ID NO: 7), or a pharmaceutically acceptable salt thereof.

in an amount effective to attract a progenitor cell to a location in a patient, and a pharmaceutically acceptable excipient. In one embodiment, the polypeptide is not (SEQ ID NO: 8). As used herein, a composition or drug product comprising an amount of a stated polypeptide(s) "effective to attract a progenitor cell to a location in a patient" means the composition or drug product contains an amount of the polypeptide(s) useful in attracting progenitor cell(s) to a location in a patient when the composition or drug product is delivered to a patient by a suitable delivery route, such as by injection, implantation or transdermally.

Compositions or drug products may comprise a pharmaceutically acceptable excipient. An excipient is an inactive substance used as a carrier for the active ingredients of a medication, though "inactive," excipients may facilitate and aid in increasing the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts (see, generally, Gerbino, P P, *Remington: The Science and Practice of Pharmacy,* 21st Edition, Lippincott Williams & Wilkins (2005)).

Useful drug products (dosage forms) include: topical ointments, salves, or creams and transdermal devices (e.g., patches or bandages). In one embodiment, the compound is a sterile solution comprising the active ingredient (drug, or compound), and a solvent, such as water, saline, lactated Ringer's solution, or phosphate-buffered saline (PBS). Additional excipients, such as polyethylene glycol, emulsifiers, salts and buffers may be included in the solution.

In one embodiment, the drug product is a transdermal device, or "patch" or bandage. The general structure of a transdermal patch is broadly known in the pharmaceutical arts. A typical patch includes, without limitation: a delivery reservoir for containing and delivering a drug product to a subject, an occlusive backing to which the reservoir is attached on a proximal side (toward the intended subject's skin) of the backing and extending beyond, typically completely surrounding the reservoir, and an adhesive on the proximal side of the backing, surrounding the reservoir, typically completely, for adhering the patch to the skin of a patient. The reservoir typically comprises a matrix formed from a non-woven (e.g., a gauze) or a hydrogel, such as a polyvinylpyrrolidone (PVP) or polyvinyl acetate (PVA), as are broadly known. The reservoir typically comprises the active ingredient absorbed into or adsorbed onto the reservoir matrix, and skin permeation enhancers. The choice of permeation enhancers typically depends on empirical studies. Certain formulations that may be useful as permeation enhancers include, without limitation: DMSO; 95% Propylene Glycol+5% Linoleic Acid; and 50% EtOH+40% HSO+5% Propylene Glycol+5% Brij30.

The drug product may be a composition absorbed into an absorbent material, such as a woven or non-woven fabric material or sponge. The fabric material may be a wound dressing, such as a gauze material or a bandage. The drug product may be a bandage comprising a composition, such as an aqueous liquid, comprising a compound described herein. Alternately, the drug product may be a liquid for absorption into an absorbant material, such as a liquid to be applied to a bandage prior to placement of a bandage on a wound of a patient.

In another embodiment, the compounds may be mixed with a carrier in the form of a paste to be applied to a location, such as a wound site, in a patient. The paste may be formulated to adhere to the wound, and may comprise a thickener, such as carboxymethylcellulose (CMC). The paste also may comprise a comminuted (chopped, powdered, crushed, divided, etc.) biological (e.g. cell growth) scaffold. A large variety of suitable biological scaffolds are known in the art. In one embodiment, the biological scaffold is a decellularized ECM-derived material, as described below. In another embodiment, the biological scaffold includes collagen and/or hyaluronic acid.

Thus, the compounds described herein can be provided in and used in any number of drug products, i.e., dosage forms and/or devices. In one embodiment, a device is prepared comprising an ECM-derived material and one or more of Peptide 1, Peptide 2, and analogs thereof described above, synthesized synthetically, as described herein. A solution comprising the peptide(s) is contacted with a sheet of a lyophilized UBM (e.g., purchased from Acell Corporation of Jessup, Md.)) until it is absorbed into the sheet. The device can then be used as a biological scaffold in a patient. For instance, it can be placed on a wound and layered to a desired thickness, and optionally affixed in place by sutures, staples, etc.

In another embodiment, the peptide(s) are mixed with comminuted ECM-derived material in an acceptable solution, comprising water and, optionally one or more additional excipient, such as a salt, a buffer, and/or a viscosity modifier to form a paste, gel or other viscous composition. In one example, the peptides are mixed in normal saline or PBS and mixed with an ECM-derived material to form a paste. The paste then can be administered to a patient externally or internally to a wound. In another embodiment, the peptide(s) are compounded into a suitable topical dosage form, such as an ointment or cream. The ointment or cream may be applied directly to a wound, such as a burn, or may be applied to a bandage for contact with a wound.

An "ECM-derived material," is a material prepared from an extracellular matrix-containing tissue. Any type of extracellular matrix tissue can be used in the methods, compositions and devices as described herein (see generally, U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666). In certain embodiments, the ECM is isolated from a vertebrate animal, for example and without limitation, from a warm blooded mammalian vertebrate animal including, but not limited to, human, monkey, pig, cow and sheep. The ECM can be derived from any organ or tissue, including without limitation, urinary bladder, intestine, liver, esophagus and dermis. In one embodiment, the ECM is isolated from a urinary bladder. The ECM may or may not include the basement membrane portion of the ECM. In certain embodiments, the ECM includes at least a portion of the basement membrane.

In another embodiment, the ECM is prepared by abrading porcine bladder tissue to remove the outer layers including both the tunica serosa and the tunica muscularis (layers G and F in FIG. 2) using a longitudinal wiping motion with a scalpel handle and moistened gauze. Following eversion of the tissue segment, the luminal portion of the tunica mucosa (layer H in FIG. 2) is delaminated from the underlying tissue using the same wiping motion. Care is taken to prevent perforation of the submucosa (layer E of FIG. 2). After these tissues are removed, the resulting ECM consists mainly of the tunica submucosa (layer E of FIG. 2).

The ECM can be sterilized by any of a number of standard methods without loss of its ability to induce endogenous tissue growth. For example, the material can be sterilized by propylene oxide or ethylene oxide treatment, gamma irradiation treatment (0.05 to 4 mRad), gas plasma sterilization, peracetic acid sterilization, or electron beam treatment. The material can also be sterilized by treatment with glutaraldehyde, which causes cross linking of the protein material, but this treatment substantially alters the material such that it is slowly resorbed or not resorbed at all and incites a different type of host remodeling which more closely resembles scar tissue formation or encapsulation rather than constructive remodeling. Cross-linking of the protein material can also be induced with carbodiimide or dehydrothermal or photooxidation methods. More typically, ECM is disinfected by immersion in 0.1% (v/v) peracetic acid (a), 4% (v/v) ethanol, and 96% (v/v) sterile water for 2 h. The ECM material is then washed twice for 15 min with PBS (pH=7.4) and twice for 15 min with deionized water.

Commercially available ECM preparations can also be used in the methods, devices and compositions described herein. In one embodiment, the ECM is derived from small intestinal submucosa or SIS. Commercially available preparations include, but are not limited to, Surgisis™, Surgisis-ES™, Stratasis™, and Stratasis-ES™ (Cook Urological Inc.; Indianapolis, Ind.) and GraftPatch™ (Organogenesis Inc.; Canton Mass.). In another embodiment, the ECM is derived from dermis. Commercially available preparations include, but are not limited to Pelvicol™ (sold as Permacol™ in Europe; Bard, Covington, Ga.), Repliform™ (Microvasive; Boston, Mass.) and Alloderm™ (LifeCell; Branchburg, N.J.). In another embodiment, the ECM is derived from urinary bladder. Commercially available preparations include, but are not limited to UBM (Acell Corporation; Jessup, Md.).

Tissue for preparation of ECM can be harvested in a large variety of ways and once harvested, a variety of portions of the harvested tissue may be used. For example and without limitation, in one embodiment, the ECM is isolated from harvested porcine urinary bladder to prepare urinary bladder matrix (UBM). Excess connective tissue and residual urine are removed from the urinary bladder. The tunica serosa, tunica muscularis externa, tunica submucosa and most of the muscularis mucosa (layers G, F, E and mostly D in FIG. 2) can be removed mechanical abrasion or by a combination of enzymatic treatment, hydration, and abrasion. Mechanical removal of these tissues can be accomplished by abrasion using a longitudinal wiping motion to remove the outer layers (particularly the abluminal smooth muscle layers) and even the luminal portions of the tunica mucosa (epithelial layers). Mechanical removal of these tissues is accomplished by removal of mesenteric tissues with, for example, Adson-Brown forceps and Metzenbaum scissors and wiping away the tunica muscularis and tunica submucosa using a longitudinal wiping motion with a scalpel handle or other rigid object wrapped in moistened gauze. The epithelial cells of the tunica mucosa (layer A of FIG. 2) can also be dissociated by soaking the tissue in a de-epithelializing solution, for example and without limitation, hypertonic saline. The resulting UBM comprises basement membrane of the tunica mucosa and the adjacent tunica propria (layers B and C of FIG. 2), which is further treated with peracetic acid, lyophilized and powdered. Additional examples are provided below and are also present in the related art.

In another embodiment, the epithelial cells can be delaminated first by first soaking the tissue in a de-epithelializing solution such as hypertonic saline, for example and without limitation, 1.0 N saline, for periods of time ranging from 10 minutes to 4 hours. Exposure to hypertonic saline solution effectively removes the epithelial cells from the underlying basement membrane. The tissue remaining after the initial delamination procedure includes epithelial basement membrane and the tissue layers abluminal to the epithelial basement membrane. This tissue is next subjected to further treatment to remove the majority of abluminal tissues but not the epithelial basement membrane. The outer serosal, adventitial, smooth muscle tissues, tunica submucosa and most of the muscularis mucosa are removed from the remaining de-epithelialized tissue by mechanical abrasion or by a combination of enzymatic treatment, hydration, and abrasion.

In one embodiment, the ECM is prepared by abrading porcine bladder tissue to remove the outer layers including both the tunica serosa and the tunica muscularis (layers G and F in FIG. 2) using a longitudinal wiping motion with a scalpel handle and moistened gauze. Following eversion of the tissue segment, the luminal portion of the tunica mucosa (layer H in FIG. 2) is delaminated from the underlying tissue using the same wiping motion. Care is taken to prevent perforation of the submucosa (layer E of FIG. 2). After these tissues are removed, the resulting ECM consists mainly of the tunica submucosa (layer E of FIG. 2).

ECM-derived material can be decelluarized, sterilized and/or dried by any useful method. ECM-derived material can then be used in any form in the methods and compositions described herein. For instance, the compounds described herein can be applied to sheets of ECM or comminuted ECM to prepare a biological scaffold suitable to apply to any location in a patient, such as a skin, cartilage, muscle, bone, or nerve growth scaffold.

As used herein, the term "polymer" refers to both synthetic polymeric components and biological polymeric components. "Biological polymer(s)" are polymers that can be obtained from biological sources, such as, without limitation, mammalian or vertebrate tissue, as in the case of certain extracellular matrix-derived (ECM-derived) compositions, described above. Biological polymers can be modified by additional processing steps. Polymer(s), in general include, for example and without limitation, mono-polymer(s), copolymer(s), polymeric blend(s), block polymer(s), block copolymer(s), cross-linked polymer(s), non-cross-linked polymer(s), linear-, branched-, comb-, star-, and/or dendrite-shaped polymer(s), where polymer(s) can be formed into any useful form, for example and without limitation, a hydrogel, a porous mesh, a fiber, woven mesh, or non-woven mesh, such as, for example and without limitation, as a non-woven mesh formed by electrospinning.

Generally, the polymeric components suitable for the scaffold described herein may be any polymer that biocompatible and can be biodegradable. By "biodegradable," it is meant that a polymer, once implanted and placed in contact with bodily fluids and/or tissues, will degrade either partially or completely through chemical, biochemical and/or enzymatic processes. Non-limiting examples of such chemical reactions include acid/base reactions, hydrolysis reactions, and enzymatic cleavage. In certain non-limiting embodiments, the biodegradable polymers may comprise homopolymers, copolymers, and/or polymeric blends comprising, without limitation, one or more of the following monomers: glycolide, lactide, caprolactone, dioxanone, and trimethylene carbonate. In other non-limiting embodiments, the polymer(s) comprise labile chemical moieties, non-limiting examples of which include esters, anhydrides, polyanhydrides, or amides, which can be useful in, for example and without limitation, controlling the degradation rate of the scaffold and/or the release rate of therapeutic agents from the scaffold. Alternatively, the polymer(s) may contain peptides or biomacromolecules as building blocks which are susceptible to chemical reactions once placed in situ. In one non-limiting example, the polymer is a polypeptide comprising the amino acid sequence alanine-alanine-lysine, which confers enzymatic lability to the polymer. In another non-limiting embodiment, the polymer composition may comprise a biomacromolecular component derived from an ECM. For example, the polymer composition may comprise the biomacromolecule collagen so that collagenase, which is present in situ, can degrade the collagen.

The polymeric components used to make the scaffold are preferably biocompatible. By "biocompatible," it is meant that a polymer compositions and its normal degradation in vivo products are cytocompatible and are substantially non-toxic and non-carcinogenic in a patient within useful, practical and/or acceptable tolerances. By "cytocompatible," it is meant that the polymer can sustain a population of cells and/or the polymer composition, device, and degradation products, thereof are not cytotoxic and/or carcinogenic within useful, practical and/or acceptable tolerances. For example, the polymer when placed in a human epithelial cell culture does not adversely affect the viability, growth, adhesion, and number of cells. In one non-limiting embodiment, the compositions, and/or devices are "biocompatible" to the extent they are acceptable for use in a human veterinary patient according to applicable regulatory standards in a given jurisdiction. In another example the biocompatible polymer, when implanted in a patient, does not cause a substantial adverse reaction or substantial harm to cells and tissues in the body, for instance, the polymer composition or device does not cause necrosis or an infection resulting in harm to tissues from the implanted scaffold.

The synthetic polymeric component can be a biocompatible, biodegradable and synthetic polymer material. Common synthetic biological scaffolds comprise PLGA (poly(lactic-co-glycolic acid)), PLG (Poly(lactide-co-glycolide)), PLA (poly(lactide)) and POE (poly(ortho esters)), or combinations thereof, which are materials commonly used in cell-growth scaffolds. Other synthetic polymeric component include a biodegradable poly(ester urethane) urea elastomer (PEUU) or a poly(ether ester urethane) urea elastomer (PEEUU). In yet another non-limiting embodiment, the synthetic polymeric component comprises any hydrolytically, chemically, biochemically, and/or proteolytically labile group, non-limiting examples of which include an ester moiety, amide moiety, anhydride moiety, specific peptide sequences, and generic peptide sequences.

In one example, the scaffold comprises a mixture of synthetic and biological polymeric components. For example, a mixture may comprise 50% of a synthetic polymeric component and 50% of a biological polymeric component, for example, the mixture may comprise 50% PEUU by weight and 50% UBM by weight.

In certain embodiments, the polymers used to make the biological scaffold are not only non-toxic and non-carcinogenic, but also release therapeutic agents when they degrade within the patient's body. For example, the individual building blocks of the polymers may be chosen such that the building blocks themselves provide a therapeutic benefit when released in situ through the degradation process. In one embodiment, one of the polymer building blocks is putrescine, which has been implicated as a substance that causes cell growth and cell differentiation.

In another embodiment, at least one additional therapeutic agent is added to the biological scaffold or composition described herein before it is implanted in the patient or otherwise administered to the patient. Generally, the therapeutic agents include any substance that can be coated on, embedded into, absorbed into, adsorbed to, or otherwise attached to or incorporated onto or into the biological scaffold or incorporated into a drug product that would provide a therapeutic benefit to a patient. Non-limiting examples of such therapeutic agents include antimicrobial agents, growth factors, emollients, retinoids, and topical steroids. Each therapeutic agent may be used alone or in combination with other therapeutic agents. For example and without limitation, a biological scaffold comprising neurotrophic agents or cells that express neurotrophic agents may be applied to a wound that is near a critical region of the central nervous system, such as the spine. Alternatively, the therapeutic agent may be blended with the polymer while a polymer is being processed. For example, the therapeutic agent may be dissolved in a solvent (e.g., DMSO) and added to the polymer blend during processing. In another embodiment, the therapeutic agent is mixed with a carrier polymer (e.g., polylactic-glycolic acid microparticles) which is subsequently processed with an elastomeric polymer. By blending the therapeutic agent with a carrier polymer or elastomeric polymer itself, the rate of release of the therapeutic agent may be controlled by the rate of polymer degradation.

In certain non-limiting embodiments, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors □□ and □ (TGF-□ and TGF-□), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minn.; Biovision, Inc, Mountain View, Calif.; ProSpec-Tany TechnoGene Ltd., Rehovot, Israel; and Cell Sciences®, Canton, Mass.

In certain non-limiting embodiments, the therapeutic agent is an antimicrobial agent, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

In certain non-limiting embodiments, the therapeutic agent is an anti-inflammatory agent, such as, without limitation, an NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin. Other drugs that may promote wound healing and/or tissue regeneration may also be included.

Biological scaffolds may be prepared by any suitable method, including by form casting, electrospinning, electrodeposition, etc. The compounds may be incorporated into a biological scaffold by any method, including absorption, adsorption, mixing, etc.

Methods of treatment of a patient, comprising administering to a location on a patient one or more polypeptide or composition described herein with the object of attracting precursor cells to the location, thereby resulting in tissue growth/repair at the location. A device, such as a patch, bandage or biological scaffold comprising a substrate, such as a biological scaffold material, comprising the compounds or compositions described herein. The substrate may be a patch, or have (e.g., be formed into) a three-dimensional shape that is suitable for the device's intended use, such as a tubular shape, for blood vessel or esophageal repair, a planar patch for skin repair, or a plug for cardiac or cartilage repair. In one embodiment, one or more polypeptides and the compositions described herein are used to enhance bone repair by attracting osteogenic (bone forming) precursor cells to a site of bone injury. As shown in the Examples below, even when the polypeptides are administered to locations in the patient other than the site of bone injury or a bone defect, the polypeptides enhance bone repair/growth at the site of injury. Thus the polypeptides can be administered at or adjacent to a site of bone injury or defect in a patient, or even remotely in the patient, to enhance repair of the bone injury or defect.

Example 1

Urinary Bladder Matrix Preparation

Porcine urinary bladders were harvested from market-weight pigs (110-130 kg) immediately after euthanasia. Urinary bladder matrix (UBM) was prepared as previously described.[30] Briefly, connective tissues were removed from the serosal surface of the bladder. The tunica serosa, tunica muscularis externa, tunica submucosa, and most of the tunica muscularis mucosa were then mechanically delaminated, and the luminal urothelial cells of the tunica mucosa were dissociated by soaking in a 1.0N saline solution. The remaining tissue consisted of only the basement membrane, the subjacent tunica propria of the tunica mucosa, and the resident cell population of those two layers. The matrix was decellularized by treating with 0.1% peracetic acid/4% ethanol for 2 h and rinsing with phosphate-buffered saline (PBS) and deionized water. Complete decellularization was confirmed using 40-6-diamidino-2-phenylindole (DAPI) nuclear staining and hematoxylin and eosin staining. The ECM was then lyophilized and frozen. The frozen ECM was comminuted into a particulate form using a Waring commercial blender and a Wiley Mill with a #60 mesh screen.[31]

Pepsin Digestion:

UBM was digested with pepsin by mixing 1 g of lyophilized, powdered UBM with 100 mg pepsin (Sigma-Aldrich, St. Louis, Mo.) in 100 mL 0.01N hydrochloric acid. This solution was stirred constantly at room temperature for 48 h, neutralized to a pH of 7.4 (pepsin is inactivated at neutral pH), and then assayed for chemotactic and mitogenic activities at doses ranging from 10 to 1000 µg dry weight/mL in the chemotactic assays and from 15.8 to 78.9 µg total protein/mL in the proliferation assays. One hundred milligrams of pepsin in 100 mL 0.01N hydrochloric acid, without UBM, was prepared in parallel, incubated for 48 h, neutralized, and used as a control in the chemotactic and proliferation assays.

Papain Digestion:

One gram of lyophilized, powdered UBM was placed in a flask containing 100 mL of PBS with 1 U/mL of papain (Sigma-Aldrich). The flask was covered to minimize evaporation, placed inside an incubator at 37° C., and kept under constant stir for a total of 24 h. After the 24 h digestion period, the solution was brought to room temperature and spun at 1000 rpm for 6 min, and the supernatant was collected. For each milliliter of solution, 1 mL of 1 mM E-64 protease inhibitor (Sigma-Aldrich) was added to inactivate the papain. 1 U/mL of papain in PBS, with no UBM, was incubated at 37° C., centrifuged, and inactivated with 1 mME-64 in parallel, and was used as a control in the chemotactic assay. Intact ECM was not used as a control with either the pepsin or papain digestion products because elution of variable amounts of intact growth factors such as vascular endothelial growth factor (VEGF) and basic fibroblast growth factor (bFGF) would add unknown variables to the experimental design.

Cell Culture:

MRL blastema cells (MRL-B cells) were isolated from the ears of MRL/MpJ mice (Jackson Laboratories, Bar Harbor, Me.). A 2.0-mm hole was punched through the ear of each mouse. The MRL/MpJ mice have been described as having exceptional healing/regenerative properties.[33] At the site of the ear hole punch in the MRL/MpJ mice, a blastema-like structure forms, and if the cells are allowed to accumulate, differentiate, and organize, then the result is ear hole closure and tissue regeneration.[34] At 11 days after creating the ear hole, there was evidence of partial closure, and cells were isolated from the healing edge of the defect. Cells were grown in Dulbecco's modified Eagle's medium (DMEM, Cat. no. D6429; Sigma-Aldrich) supplemented with 10% fetal calf serum (FCS), 2 mM glutamine, 100 U/mL penicillin, and 100 mg/mL streptomycin in 95% air/5% $CO_2$ at 37° C.

Multilineage progenitor cells (MLPCs), a primary cell line of human umbilical cord blood origin that is capable of differentiation into cell types representing the three germinal layers, were purchased from BioE (St. Paul, Minn.) and cultured in mesenchymal stem cell growth medium (MSCGM) (Cambrex, East Rutherford, N.J.) under a humidified atmosphere in 95% air/5% $CO_2$ at 37° C.

Figure 3:
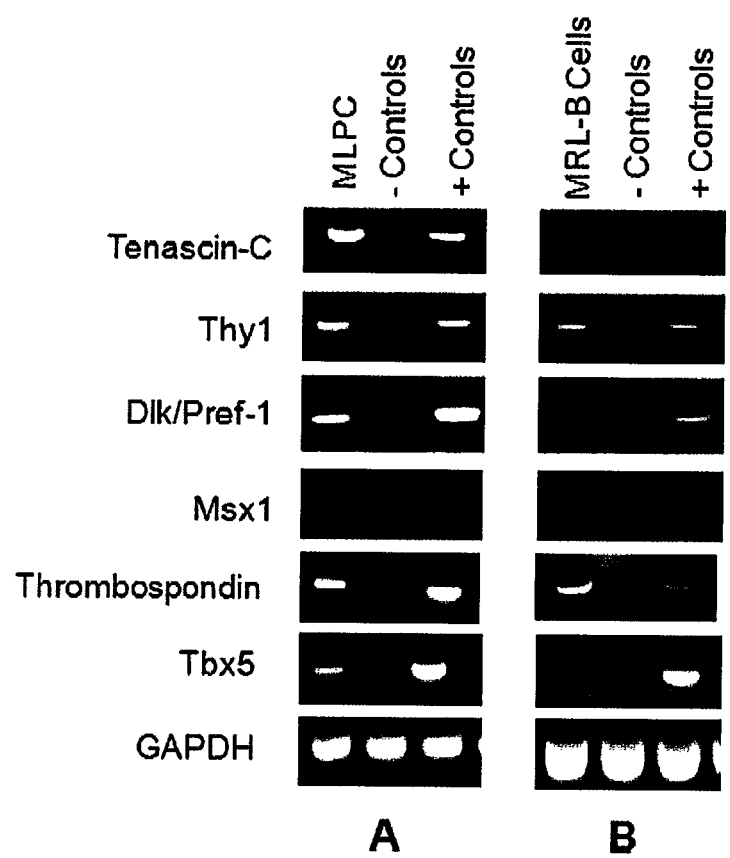
FIG. 3 are photographs of gels showing both multilineage progenitor cells (MLPCs) and MRL day 11 blastema cells (MRL-B cells) were positive for all genes of interest when compared to the cell lines or tissue controls listed in Table 2. RNA was extracted and reverse transcribed for (A) MLPC and (B) MRL-B cells. The resulting cDNA was screened via PCR for Tenascin-C, Thy1, Dlk/Pref-1, Msx1, Thrombospondin, and Tbx5.

Both MLPC and MRL-B cells are positive for molecules associated with progenitor cell status and with tissue regeneration. Specifically, both cell populations showed expression of Tenascin-C, Thy1, Dlk/Pref-1, Msx1, Thrombospondin, and Tbx5 (FIG. 3 and Table 1).

In Table 3, primers for Tbx5, Dlk/Pref-1 (Dlk), Msx1, Thrombospondin (THBS), Tenascin-C (TnC), Thy1, and glyceraldehyde 3-phosphate dehydrogenase (GAPDH) were purchased from Operon Biotechnologies (Huntsville, Ala.). *Primers that were designed using the PrimerQuest software from Integrated DNA Technologies (Coralville, Iowa) and verified by BLAST sequencing. All primer sets span intronic sequences as an added quality control step. Cell lines used as controls included the mouse fibroblast cell line NIH-3T3 and the human breast cancer cell line MCF-7.

Human aortic endothelial cells (HAEC), human microvascular endothelial cells from bladder (HMVEC-bladder), and human microvascular endothelial cells from lung (HMVEClung) were purchased from Lonza (Walkersville, Md.). HAEC were cultured in EGM2 medium (Lonza) under a humidified atmosphere in 95% air/5% $CO_2$ at 37° C.; HMVEC-bladder and HMVEC-lung were cultured in EGM2-MV medium (Lonza) under a humidified atmosphere in 95% air/5% $CO_2$ at 37° C. Capillary endothelial cells from a primary cell line of bovine adrenal cortex (bovine endothelial cells, or BEC) were purchased from Lonza and cultured in EGM2-MV medium with a bullet kit CC-3202 (Lonza) and a

TABLE 1

Primer Sequences Used for Cell Characterization

| Gene | Sequence (5' to 3')(SEQ ID NO) | Band size (bp) | +Control | -Control |
|---|---|---|---|---|
| Mouse | | | | |
| TnC | F: CGGATCCGTTTGGAGACCGCACAGAAGAA (16)<br>R: CGCAAGCTTTGTCCCCATATCTGCCCATCA (17) | 365 | NIH-3T3 | Spleen |
| Thy1 | F: CAAGGTCCTTACCCTAGCCAA (18)<br>R: CCAGCTTGTCTCTATACACACTG (19) | 125 | NIH-3T3 | Lung |
| Dlk | F: ACAATGTCTGCAGGTGCCATGTTG (20)<br>R: AGGAGCATTCGTACTGGCCTTTCT (21) | 224 | NIH-3T3 | |
| Msx1 | F: CTCTCGGCCATTTCTCAGTC (22)<br>R: TACTGCTTCTGGCGGAACTT (23) | 246 | Brain | NIH-3T3 |
| THBS | F: ATCGCGAAGCTGCTATCCAGTTCT (24)<br>R: TCTTCATCTGCCTCAAGGAAGCCA (25) | 457 | NIH-3T3 | Heart |
| Tbx5 | F: ATATTGTTCCCGCAGACGACCACA (26)<br>R: TAATGTGTCCAAACGGGTCCAGGT (27) | 200 | Heart | Brain |
| GAPDH | F: CGCAACGACCCCTTCATTGACC (28)<br>R: CGATGAGCCCTTCCACAATGCC (29) | 432 | | |
| Human | | | | |
| TnC | F: AGATGTCACAGACACCACTGCCTT (30)<br>R: TGTGGCTTGTTGGCTCTTTGGAAC (31) | 405 | Liver | MCF-7 |
| Thy1 | F: CCCGAACCAACTTCACCAGCAAAT (32)<br>R: TCTCTGCACTGGAACTTGAGGCTT (33) | 310 | Liver | MCF-7 |
| Dlk | F: CTGGACGATGGCCTCTATGAATG (34)<br>R: ATCATCCACGCAGGTGCCTC (35) | 125 | Liver | MCF-7 |
| Msx1 | F: TCCTCAAGCTGCCAGAAGAT (36)<br>R: ACGGTTCGTCTTGTGTTTGC (37) | 151 | MCF-7 | Liver |
| THBS | F: TGACAAGGACAACTGCAGACTCGT (38)<br>R: AGGAATCATCTGGAATCGGCGGAA (39) | 177 | Liver | Heart |
| Tbx5 | F: ACATTGTACCTGCCGACGATCACA (40)<br>R: AGACGTGAGTGCAGAACGGCTTAT (41) | 302 | Heart | Liver |
| GAPDH | F: GAAGGTGAAGGTCGGAGTC (42)<br>R: GAAGATGGTGATGGGATTTC (43) | ~250 | | | final FCS concentration of 5%. For proliferation assays, cells were plated in 48-well plates at 1000 cells/well in EGM2-MV medium with 10% FCS (JRH Biosciences, Lenexa, Kans.) supplemented with 2 mM glutamine, 100 U/mL penicillin, 100 µg/mL streptomycin (GPS; Irvine Scientific, Santa Ana, Calif.), and 2 µg/mL Fungizone (Fisher Scientific, Pittsburgh, Pa.), without added growth factors under a humidified atmosphere of 95% air/5% $CO_2$ at 37° C.

RNA Isolation and Analysis:

Mouse MRL-B cells and human MLPC were grown to at least 50% confluency in 75 $cm^2$ flasks, collected, and lysed. Total RNA was extracted using the Qiagen RNeasy Kit (Qiagen, Valencia, Calif.) according to the manufacturer's instructions with the recommended DNase treatment for removal of genomic DNA. RNA concentrations were determined by measuring absorbance at 260 nm on a BioMate3 spectrophotometer (Thermo Spectronic, Rochester, N.Y.). Control RNA samples from human and mouse tissues were prepared by homogenization in TriReagent and chloroform extraction; RNA was extracted from aqueous phase using Qiagen RNeasy Kit as detailed above. First-strand cDNA was synthesized from 1 µg of RNA using the Superscript First-Strand Synthesis System (Invitrogen, Carlsbad, Calif.) according to the manufacturer's instructions. PCR was performed with primers specific for Tbx5, Dlk/Pref-1 (Dlk), Msx1, Thy1, Thrombospondin (THBS), Tenascin-C (TnC), and glyceraldehyde 3-phosphate dehydrogenase (GAPDH) (Table 2). cDNAs were amplified in EasyStart Micro100 tubes (Molecular BioProducts, San Diego, Calif.) with 100 nM of primer in a Mastercycler (Eppendorf, Westbury, N.Y.). All PCR runs were 35 cycles. PCR products were separated on 2% agarose gels, stained with ethidium bromide, and visualized on Kodak Image Station 2000R (Kodak, Rochester, N.Y.).

Neuro Probe Chamber Chemotaxis Assay:

Responses of MRL-B cells and endothelial cells to ECM degradation products were quantitatively evaluated utilizing the Neuro Probe 48-well microchemotaxis chamber (Neuro Probe, Gaithersburg, Md.). Cells to be assayed for migration response were starved for 14-17 h in media with no added growth factors containing 0.5% heat-inactivated FCS. The starved cells were harvested with trypsin, resuspended in serum-free media at a concentration of $6 \times 10^5$ cells/mL, and preincubated for 1 h in a humidified 95% air/5% $CO_2$ 37° C. incubator. Polycarbonate chemotaxis filters (Neuro Probe, Gaithersburg, Md.), 8 µm pore size filters (Neuro Probe PFB8) for endothelial cells and 12 µm pore size filters (Neuro Probe PFB12) for MRL-B cells, were coated equally on both sides (by immersion) with 0.05 mg/mL collagen 1 (BD Biosciences, San Jose, Calif.). The ECM degradation products collected from the pepsin or papain digestion were added to the bottom chamber wells (see Table 2 for optimum concentrations), the filter was placed over the bottom chamber, and the apparatus was assembled according to the manufacturer's instructions. Approximately 30,000 cells were then added to each upper chamber well of the apparatus, and the chamber was incubated for 3 h at 37° C. under a humidified atmosphere in 95% air/5% $CO_2$. Cells remaining on the topside of the membrane (i.e., nonmigrated cells) were removed, and then cells on the bottom side of the membrane (i.e., migrated cells) were stained with Diff Quik (Dade AG, Liederbach, Germany). Three predetermined fields were counted from each well at 20× magnification. Fields were predetermined by location in the well: cells in the top left, top right, and bottom center fields in each well were counted. Each experimental condition was tested in quadruplicate wells, and the average number of migrated cells was determined for each condition.

The Student's t-test was used to test the null hypothesis that there was no difference between the results of cell migration toward each ECM degradation product and the appropriate control buffer. p-values≤0.05 were considered significant.

TABLE 2

The Cell Types and ECM Digests That Were Evaluated in Migration and Proliferation Assays Are Listed

| | Assay | | |
|---|---|---|---|
| Digestion Method | Neuro Probe chamber migration assay | Fluorescence-based migration assay | Proliferation assay |
| Pepsin | MRL-B<br>HAEC<br>HMVEC-bladder<br>HMVEC-lung | MRL-B<br>MLPC | MRL-B<br>BEC |
| Papain | MRL-B<br>HAEC<br>HMVEC-bladder<br>HMVEC-lung | | |

Cell types assayed included MRL blastema cells (MRL-B), multilineage progenitor cells (MLPCs), human aortic endothelial cells (HAEC), human microvascular endothelial cells from bladder and lung (HMVEC-bladder and HMVEC-lung, respectively), and bovine adrenal capillary endothelial cells (BEC). Concentrations of ECM digests used in these assays were as follows: ECM-pepsin digest, 200-500 µg dry weight/mL for Neuro Probe 48-well microchemotaxis chamber migration assay, 1 mg dry weight/mL for fluorescence based migration assay, and 78.9 µg total protein/mL for proliferation assay; ECM-papain digest, 500 lag total protein/mL for Neuro Probe chamber migration assay.

Figure 4:
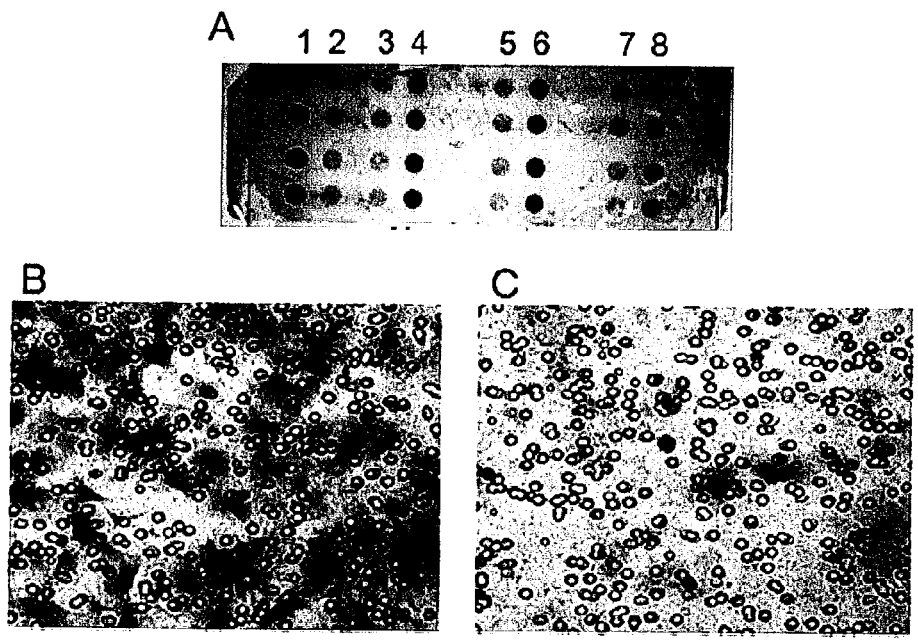
FIG. 4 (A) Photograph of the filter from a Neuro Probe assay testing the migration of MRL-B cells toward three protein concentrations of UBM papain digest. Well-shaped areas visible by eye on the filter correspond to wells containing migrated, stained cells. This assay was run in quadruplicate, with four wells for each test sample or control. Samples placed in bottom chamber wells for this assay were as follows: row 1, positive control (10% fetal bovine serum); row 2, negative control (DMEM); rows 3, 5, and 7, control buffers for 500, 200, and 100 µg/mL UBM papain digests, respectively; rows 4, 6, and 8, 500, 200, and 100 µg/mL UBM papain digests, respectively. Actual quantitative results for the assay were evaluated by counting the cells. (B) and (C) are photographs of Diff Quik-stained cells on the filters, for wells containing 200 µg/mL UBM papain (B) and papain control buffer for 200 µg/mL (C).

Pilot studies were conducted to determine optimal concentrations of ECM degradation products for the Neuro Probe chemotaxis assay. A range of concentrations for each ECM preparation was tested: UBM pepsin digest was tested at concentrations ranging from 10 to 200 µg/mL dry weight; UBM papain digest was tested at concentrations ranging from 100 to 500 µg/mL protein. The appropriate filter pore size for each cell type was determined by conducting pilot studies to measure the migration of the cells toward positive control chemoattractants and negative controls in the Neuro Probe chamber. Filters with pore sizes of 5, 8, and 12 µm were included in these pilot studies. FIG. 4A shows a representative filter from a Neuro Probe chemotaxis assay, and FIGS. 4B and 4C show photographs of migrated cells from that filter. The photograph of the filter is from the bottom side of the filter after cells have been scraped from the topside. This particular assay measured MRL-B cell migration toward a range of UBM papain digest concentrations.

Fluorescence-Based Migration Assay:

Responses of MRL-B cells and MLPC to UBM pepsin digest were quantitatively evaluated utilizing the 8 mm CytoSelect™ cell migration assay (Cell Biolabs, San Diego, Calif.). Cells to be assayed for migration response were starved for 14-17 h in media with no added growth factors containing 0.5% heat inactivated FCS. The starved cells were harvested with trypsin, resuspended in serum-free media at a concentration of $4 \times 10^5$ cells/mL, and preincubated for 1 h in a humidified 95% air/5% $CO_2$ 37° C. incubator. While cells were preincubating, 150 µL of UBM pepsin digest or buffer control was added to each well of the 96-well feeder tray (see Table 1 for optimum concentrations). The 96-well membrane chamber insert was placed onto the feeder tray, and 100 µL of cell suspension was added to each well of the membrane chamber, for a final concentration of 40,000 cells per well. The plate was covered and incubated for 4 h at 37° C. under a humidified atmosphere in 95% air/5% $CO_2$. One hundred and fifty microliters of cell detachment solution was added to each well of a clean harvesting tray. The 96-well membrane chamber was separated from the feeder tray, remaining cells on the topside of the membrane chamber were removed by aspiration, and the membrane chamber was placed onto the harvesting tray containing cell detachment solution and incubated in a cell culture incubator for 1 h, rinsing any cells from the bottom of the membranes into the harvesting tray wells. CyQuant GR Dye/cell lysis solution was prepared by diluting the dye in lysis buffer (1:75), the membrane chamber was removed from the harvesting tray, and 50 µL of dye/cell lysis solution was added to each well of the harvesting tray. The tray was incubated at room temperature for 20 min in order to lyse the cells and stain the nucleic acids. One hundred and fifty microliters of the contents of each well was then transferred to a plate suitable for fluorescence measurement. Fluorescence was measured with a SpectraMax M2 Plate Reader (Molecular Devices, Sunnyvale, Calif.) at 480/520 nm. Each experimental condition was tested in triplicate, and the average number of migrated cells was determined for each condition. The Student's t-test was used to detect significant differences between the results of cell migration toward each ECM degradation product and the appropriate control buffer. p-values≤0.05 were considered significant.

Proliferation Assay:

Quantitative measurement of MRL-B and capillary endothelial cell proliferation was determined in a cell proliferation assay. Cells were plated in their media without growth factor additions at 1000 cells per well in a 48-well plate. Twenty four hours later, media was removed, the cells were washed, and media was replenished. At the time of media replenishment, either ECM degradation product or an identical volume of control buffer was added at varying doses to each well in triplicate. Time zero cell counts were determined in three of the wells using trypsinization and electronic cell counting with the Z1 Particle Counter (Beckman Coulter, Fullerton, Calif.). Three or 6 days after sample additions, cells in triplicate wells for control and each treatment group were trypsinized and counted (Z1 Particle Counter electronic counts). The mean value and standard deviation were determined for each condition. The Student's t-test was used to test the null hypothesis that there was no difference between the results of cell growth for cells grown in the presence of ECM degradation products and those that were grown in the presence of buffer controls.

Results

Figure 5:
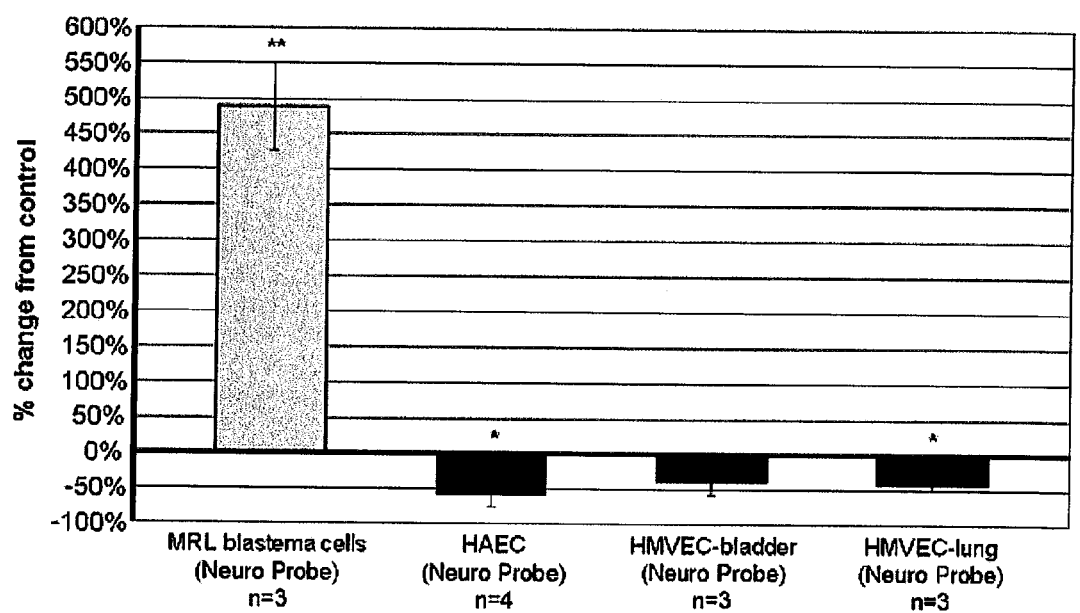
FIG. 5. UBM papain digest was chemotactic for MRL blastema cells and was chemoinhibitory for human aortic endothelial cells (HAEC) and human microvascular endothelial cells (HMVEC). Cell migration responses to 500 µg total protein/mL of papain-digested UBM were measured in the Neuro Probe 48-well microchemotaxis chamber. In the comparison of cell migration toward the UBM papain digest and cell migration toward the control buffer, double asterisks (**) signify a $p \leq 0.01$ and asterisk (*) signifies a $p \leq 0.05$.

The UBM papain digest was chemotactic for MRL-B cells (p≤0.01) and inhibited the migration of the endothelial cells HAEC (p≤0.05) and HMVEC-lung (p≤0.05) (FIG. 5). The migration of MRL-B cells toward UBM papain digest was fivefold increased over migration toward papain digest control buffer: the percent increase from control (average of three experiments) was 489% (p≤0.01). Migration of both types of endothelial cells toward papain was decreased compared to migration toward papain digest control buffer. The decrease was 57% for HAEC (average of four experiments) (p≤0.05) and was 42% for HMVEC-lung (average of three experiments) (p≤0.05).

Figure 6:
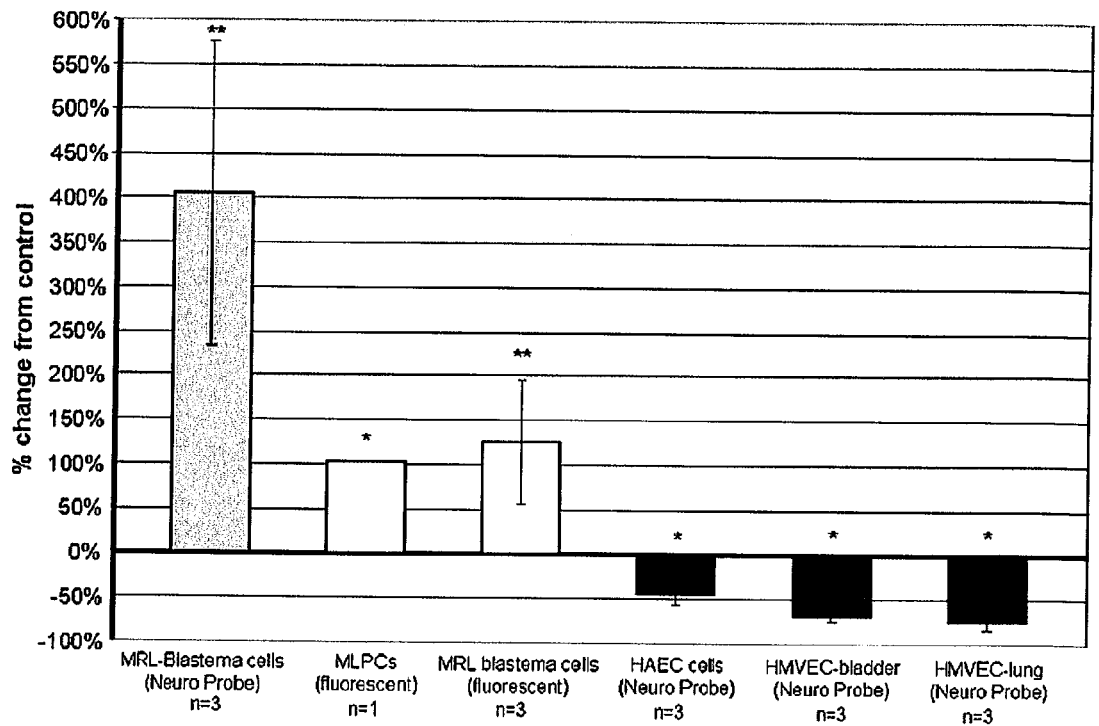
FIG. 6. UBM pepsin digest was chemotactic for MRL blastema cells and for multilineage progenitor cells (MLPCs) and was chemoinhibitory for human aortic endothelial cells (HAEC) and for human microvascular endothelial cells (HMVEC-bladder and HMVEC-lung). Cell migration responses to pepsin-digested UBM were measured with either the Neuro Probe 48-well microchemotaxis chamber or the fluorescence-based migration assay. In the comparisons of cell migration toward pepsin digest and cell migration toward control buffer, double asterisks (**) signify a $p \leq 0.01$ and asterisk (*) signifies a $p \leq 0.05$.

In a pattern similar to that observed for papain-digested UBM, the UBM pepsin digest was chemotactic for progenitor cells and inhibited the migration of endothelial cells (FIG. 6). UBM digested with pepsin enhanced the migration of MRL-B cells in both the Neuro Probe microchemotaxis chamber (405% increase from control) (p≤0.01) and fluorescencebased filter migration assays (126% increase from control) (p≤0.01), and enhanced the migration of MLPCs in the fluorescence-based migration assay (104% increase from control) (p≤0.05). The migration response of MLPCs was tested only in the fluorescence-based migration assay because the MLPCs grow slowly and there were not enough cells available for the Neuro Probe chamber assay. This same UBM pepsin digest inhibited the migration of endothelial cells. Migration toward UBM pepsin digest compared to migration toward control buffer for HAEC, HMVEC-bladder, and HMVEC-lung was decreased 44%, 70%, and 73%, respectively (all p-values≤0.05).

Table 3 provides a summary of the migration experiments performed in the Neuro Probe assay and describes the data both in terms of numbers of migrated cells counted per well and percent change from the control. Degradation products of UBM-ECM as a result of pepsin digestion were also evaluated in a quantitative assay of cell proliferation. The UBM pepsin degradation products enhanced proliferation of cells and decreased the proliferation of capillary endothelial cells (FIG. 7) (p≤0.05 for MRL-B cells and p≤0.01 for capillary endothelial cells). The proliferation assay with UBM pepsin degradation products was conducted as both a 3-day and a 6-day assay for MRL-B cells. The results for the 3-day assay are shown in FIG. 6. The UBM pepsin degradation products enhanced proliferation of MRL-B cells in both assays: in the 3-day proliferation assay, the UBM pepsin degradation products enhanced proliferation of MRL-B cells showing a 67% increase over the PBS control (p≤0.05) (FIG. 7), and in the 6-day proliferation assay, the UBM pepsin degradation products again enhanced the proliferation of MRL-B cells, showing a 50% increase over the PBS control (p≤0.01).

TABLE 3

A Summary of Neuro Probe Assay Results Is Reported Both as Average Number of Migrated Cells Counted per Well and as Average Percent Change from Controls

| Cell type | Average number of migrated cells per well | | Average % change from control | n | Average number of migrated cells per well | | Average % change from control | n |
|---|---|---|---|---|---|---|---|---|
| | UBM papain | Papain control buffer | | | UBM pepsin | Pepsin control buffer | | |
| MRL-B | 154 | 26 | 489%* | 3 | 55 | 3 | 405%* | 3 |
| HAEC | 35 | 82 | −57%** | 4 | 43 | 80 | −44%** | 3 |
| HMVEC-bladder | 35 | 63 | −39% | 3 | 18 | 61 | −70%** | 3 |
| HMVEC-lung | 76 | 134 | −42%** | 3 | 32 | 125 | −73%** | 3 |

Each experiment was set up in either triplicate or quadruplicate wells. n is the number of experiments conducted for each cell type and ECM digest combination. Percent change from control is calculated as the % change in migration of cells toward the pepsin or papain digest compared to migration of cells toward the appropriate buffer control. *$p \leq 0.01$; **$p \leq 0.05$.

Figure 7:
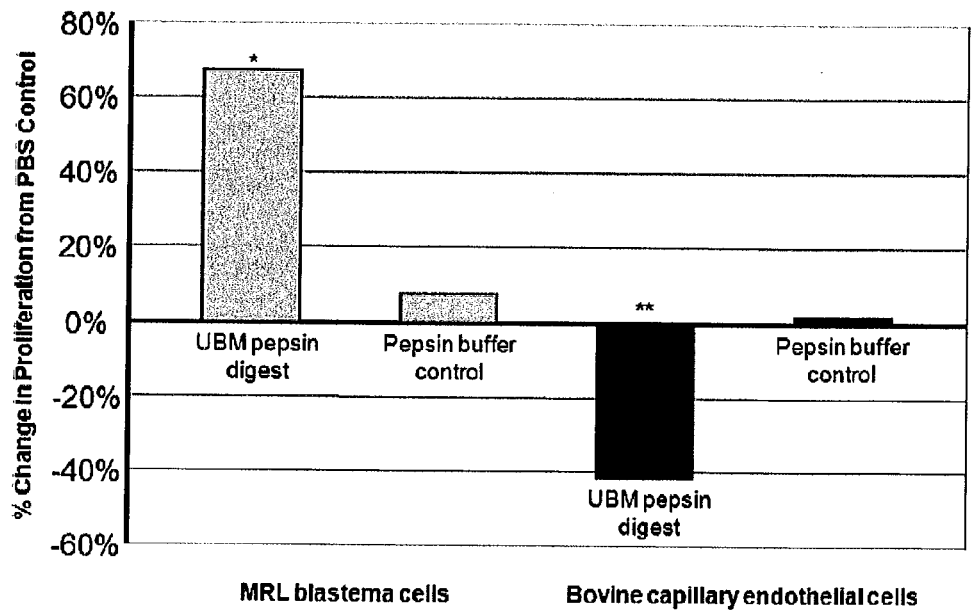
FIG. 7 UBM pepsin digest enhanced the proliferation of MRL blastema cells and inhibited the proliferation of bovine capillary endothelial cells. Cell proliferation responses to 78.9 µg protein/mL of pepsin-digested UBM were measured in a 3-day proliferation assay. In the comparison of cell proliferation in the presence of pepsin digest compared to cell proliferation in the presence of PBS alone, asterisk (*) signifies a $p \leq 0.05$ and double asterisks (**) signify a $p \leq 0.01$.
Figure 11A:
Figure 11B:
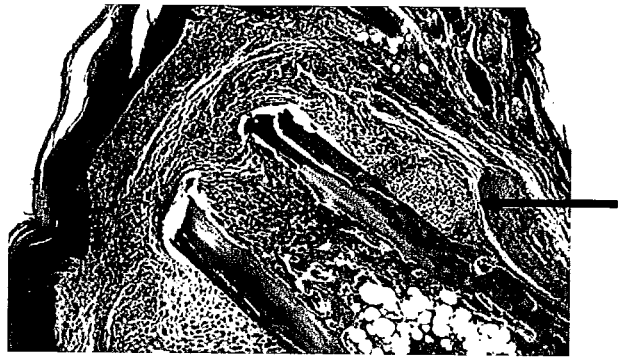
Figure 11C:
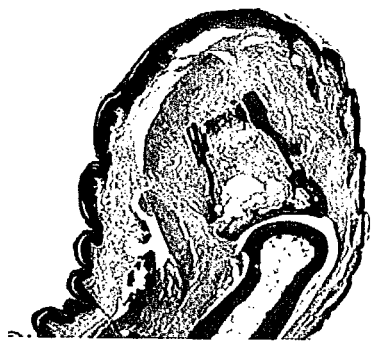
Figure 11D:
Figure 11E:
Figure 11F:
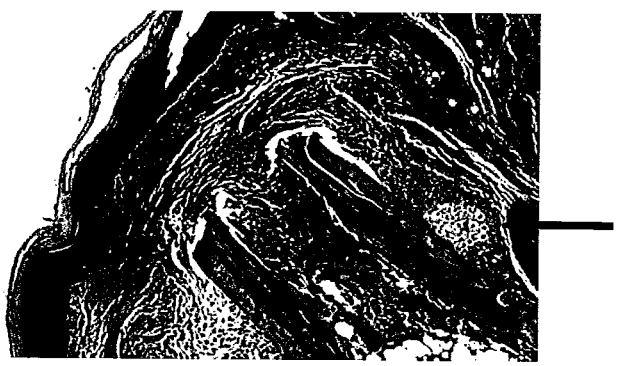

The 3-day proliferation assay with UBM pepsin degradation products was conducted three separate times for the capillary endothelial cells, in either triplicate or sextuplicate for each assay. In all three assays the UBM pepsin degradation products inhibited the proliferation of capillary endothelial cells. For the three assays, the decreases in proliferation from the PBS control for bovine capillary endothelial cells grown in the presence of UBM pepsin digest were −32% ($p \leq 0.05$), −42% ($p \leq 0.01$), and −66% ($p \leq 0.01$). A representative proliferation assay demonstrating the inhibitory effect of UBM pepsin digest on the proliferation of capillary endothelial cells is shown in FIG. 7.

Example 2

Concentrated peptides from pepsin digested UBM, prepared as described in Example 1 were fractionated by size exclusion chromatography. In further detail, peptides of pepsin-digested UBM that were prepared as described in Example 1 were fractionated via ammonium sulfate precipitation to remove viscosity, with molecules in the 0-20% cut of ammonium sulfate discarded. The remaining 20-80% ammonium sulfate cut was isolated, dialyzed into PBS and concentrated via centrifugal filtration using Amicon Ultra-4 devices. Concentrated protein was injected and fractionated via two G3000SWXL (Tosoh) HPLC size exclusion columns in series protected via a TSK-gel guard column at 0.5 ml/min. Eluent was collected and analyzed for protein via BCA assay (Thermo) and analyzed for protein abundance and chemotactic ability, revealing both chemotactic-promoting and chemotactic-inhibiting effects. Results are shown in FIG. 8. (Note. The cells that were used for the migration assay were Perivascular stem cells, the same cells that are described below).

Example 3

Post size exclusion chromatography peptide fractions that contained chemotactic ability were selected for further fractionation. Chemotactic fractions were pooled and adjusted to pH 8.8 in 50 mM Tris buffer and loaded onto a 1 ml HiTrap Q size exclusion column at 0.5 ml/min. Bound peptides were washed in buffer (50 mM Tris, pH 8.8), before fractionation using 200, 400, 500, 600, 700, 800, and 1000 mM salt cuts in the same buffer. Factions were dialyzed into PBS, and analyzed for protein abundance and chemotactic ability. Fractions revealing chemotactic ability were concentrated via centrifugal filtration and further fractionated using reverse phase chromatography. Peptides were injected onto an Octadecyl 4PW reverse phase column (Tosoh) and eluted over a 0-80% gradient of methanol in 10 mM ammonium carbonate buffer at 0.5 ml/min. Fractions were concentrated via centrifugal evaporation, resuspended in $H_2O$, and analyzed for protein abundance and chemotactic ability. Two fractionated peptides (peptides 1 and 2) that revealed chemotactic ability were sequenced via mass spectrometry and chemically synthesized. Synthesized peptides revealed chemotactic potential (See Example 4).

Example 4

To confirm the chemotactic activity for progenitor cells within ECM degradation products, human perivascular stem cells were assessed in vitro in a Boyden chamber. The peptides IAGVGGEKSGGF (Peptide 1, SEQ ID NO: 1) and GPVGPSGPPGK (Peptide 2, SEQ ID NO: 2) were tested.

Perivascular stem cells were isolated from human muscle and propagated in culture as previously described (Crisan M, Yap S, Casteilla L, et al. A perivascular origin for mesenchymal stem cells in multiple human organs. Cell Stem Cell. 2008; 3:301-313).

Perivascular stem cells were cultured in Dulbecco's Modified Eagle's Medium (DMEM) supplemented with 20% fetal calf serum (FCS), 2 mM glutamine, 100 U/ml penicillin, and 100 µg/ml streptomycin in 95% $O_2$/5% $CO_2$ at 37° C.

Cultures at passages 10-12 and 50-70% confluence were starved in serum-free DMEM supplemented with 0.5% heat inactivated (FCS) for 14-17 hours. After starvation, cells were harvested in 0.25% trypsin and 0.53 mM EDTA, centrifuged, and resuspended in DMEM with 0.5% heat inactivated FCS at a concentration of $6 \times 10^5$ cells/ml for 1 hour. Polycarbonate PFB filters (Neuro Probe, Gaithersburg, Md.) with pore size 8 µm were coated with 0.05 mg/ml Collagen Type I (BD Biosciences, San Jose, Calif.). ECM degradation products were placed in the bottom chamber of Neuro Probe 48-well chemotaxis chambers at varying concentrations (Neuro Probe, Gaithersburg, Md.), and the filter was then placed over the bottom chamber. The upper chamber was then assembled onto the lower chamber and sealed. Approximately $3 \times 10^4$ cells were placed in to each well of the top chamber, and the entire system was placed in a humidified environment at 37° C. in 95% $O_2$/5% $CO_2$. After 3 hours, cells facing the upper chamber on the filter were scraped off, and cells facing the bottom filter were fixed in methanol, stained with 500 nM DAPI (Sigma, D9564), and counted using ImageJ (NIH). FIGS. 9 and 10 show these results for Peptides 1 and 2, respectively. These results indicate excellent chemotactic activity for progenitor cells for peptides 1 and 2.

Example 5

Animal Model of Digit Amputation: Adult female 6- to 8-week-old C57/BL6 mice (n=4) were subjected to aseptic midsecond phalanx amputation of the third digit on both hind feet. At 0, 24, and 96 h after surgery 15 µL of 10 mM peptide 1 was injected into the footpad below the amputated digit using a 30-gauge needle. A second group of animals (n=4) were treated in the same way except that phosphate buffered saline (PBS) was injected instead of the peptide. Animals were killed via cervical dislocation under isoflurane anesthesia at 14 days after surgery. Isolated toes were fixed in 10% neutral buffered formalin (NBF), embedded in paraffin and cut into 5 µm sections, before deparaffinization and staining with Alcian blue at pH 2.5, hematoxylin and eosin (H&E) or Masson's trichrome.

Source of Cells and Culture Conditions: Human perivascular stem cells were obtained as described above and were cultured in high-glucose Dulbecco's modified Eagle's medium (DMEM, Invitrogen) containing 20% fetal bovine serum (FBS; Thermo), 100 U/mL penicillin, and 100 µg/mL streptomycin (Sigma) at 37° C. in 5% $CO_2$. Human cortical neuroepithelium stem (CTX) cells were cultured in DMEM: F12 supplemented with 0.03% Human albumin solution, 100 µg/ml human Apo-Transferrin, 16.2 µg/ml Putrescine DiHCl, 5 µg/ml Insulin, 60 ng/ml Progesterone, 2 mM L-Glutamine, 40 ng/ml Sodium Selinite, 10 ng/ml human bFGF, 20 ng/ml human Epidermal growth factor, and 100 nM 4-Hydroxytestosterone.

Human Perivascular Stem Cells Osteogenic Differentiation: Confluent perivascular stem cells were cultured in osteogenic differentiation medium (DMEM with 20% FBS, 20 μM ascorbic acid and 1.76 mM β-glycophosphate) and analyzed for the presence of calcium deposits after 4, 7, and 14 days. Calcium deposits were detected via fixation in 10% NBF and staining with 2% Alizarin Red.

CTX Cells Chemotaxis Assay: CTX cells (human cortical neuroepithelium stem cells) were grown to ~80% confluence, made into a single cell suspension, and the migration of $3\times10^4$ cells per well towards peptide 1 was assayed over 5 h. Migrated cells were stained by 4',6-diamidino-2-phenylindole and quantified with ImageJ (NIH). All of the data are means of quadruplicate determinations with standard deviations. The assay was performed on three separate occasions.

Results

In vivo Bone Formation: The ability of the isolated peptide to cause the development of bone in the amputated digit was analyzed by the injection of either peptide 1 or buffer into the footpad of a mouse with an amputated third digit. Injection of peptide caused the formation of a bone like growth on the side of the amputated digit that was not observed in the buffer treated group (FIG. 11). Staining of the sections with Alcian blue to detect the presence of sulfated glycosaminoglycans (GAG) revealed the presence of diffuse GAG positive staining in the buffer treated group (FIG. 12A), but concentrated GAG positive staining only at the bone nodule in the peptide treated group (FIG. 12B) confirming the change in healing response caused by the addition of the peptide.

Figure 13A:
FIGS. 13A-F are photomicrographs showing that Peptide 1 causes osteogenic differentiation of stem cells. Perivascular stem cells were cultured in osteogenic differentiation medium with (FIG. 13A) 0, (FIG. 13B) 1 µM peptide, (FIG. 13C) 10 µM peptide or (FIG. 13D) 100 µM peptide, or in standard culture medium with (FIG. 13E) 0, or (FIG. 13F) 100 µM peptide.
Figure 13B:
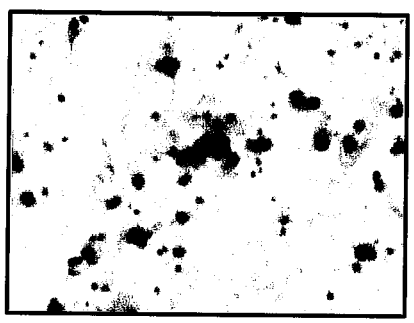
Figure 13C:
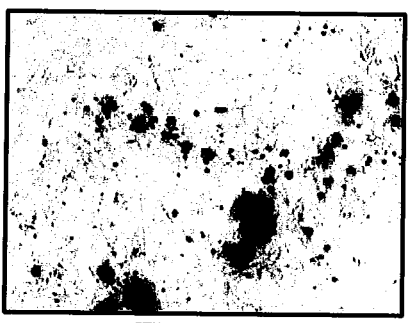
Figure 13D:
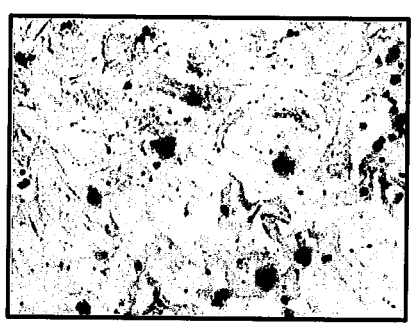
Figure 13E:
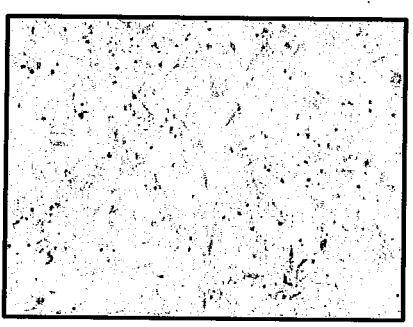
Figure 13F:
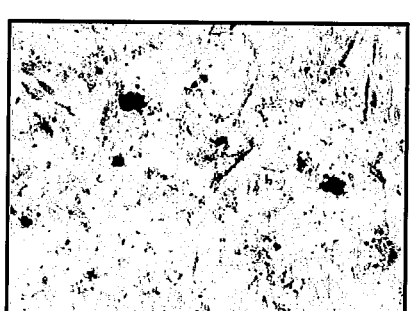
Figure 14:
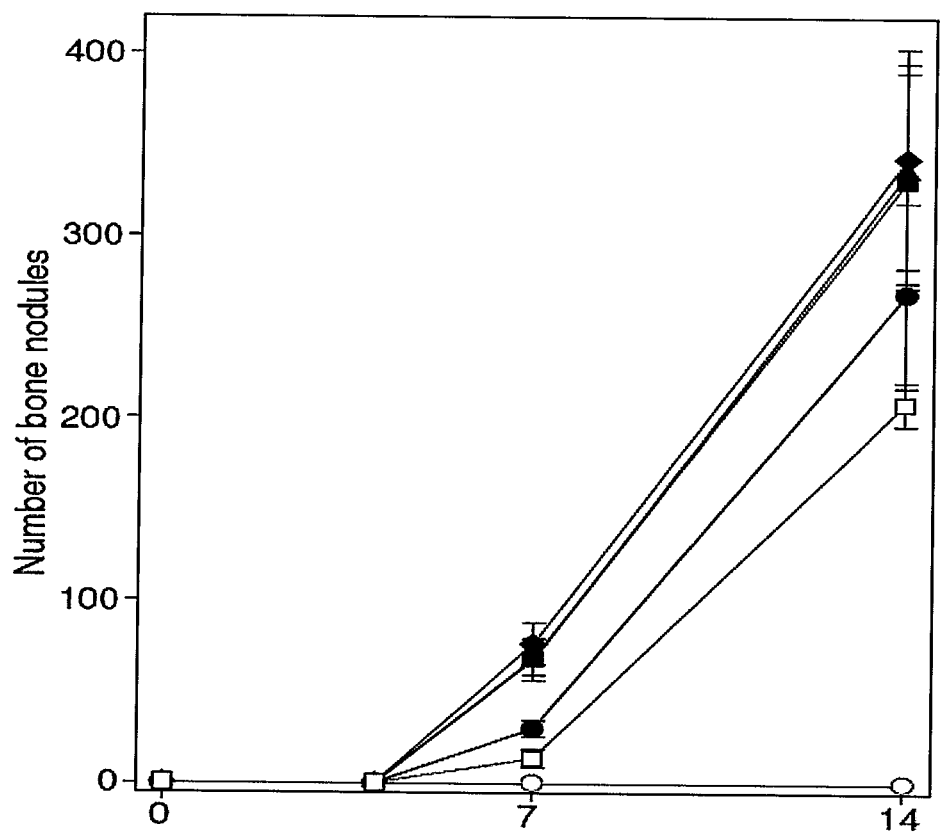
FIG. 14 is a graph showing that Peptide 1 causes osteogenic differentiation of stem cells. Perivascular stem cells were cultured in osteogenic differentiation medium (black symbols) or standard culture medium (white symbols) in the presence of 0 (circles), 1 µM (triangles), 10 µM (diamonds) or 100 µM (squares) peptide. The average number of bone nodules in three 100× fields per condition were quantified. Errors bars are SEM.

In vitro Osteogenic Differentiation: Peptide 1 was tested for its ability to cause in vitro osteogenic differentiation (FIGS. 13 and 14). Perivascular stem cells incubated in osteogenic differentiation medium and peptide resulted in more bone nodules than if incubated in differentiation medium alone (FIG. 14). Incubation of stem cells in the presence of peptide and standard culture medium also caused the formation of bone nodules (FIGS. 13F and 14) which is not seen in standard culture medium without peptide (FIGS. 13E and 14).

Figure 15:
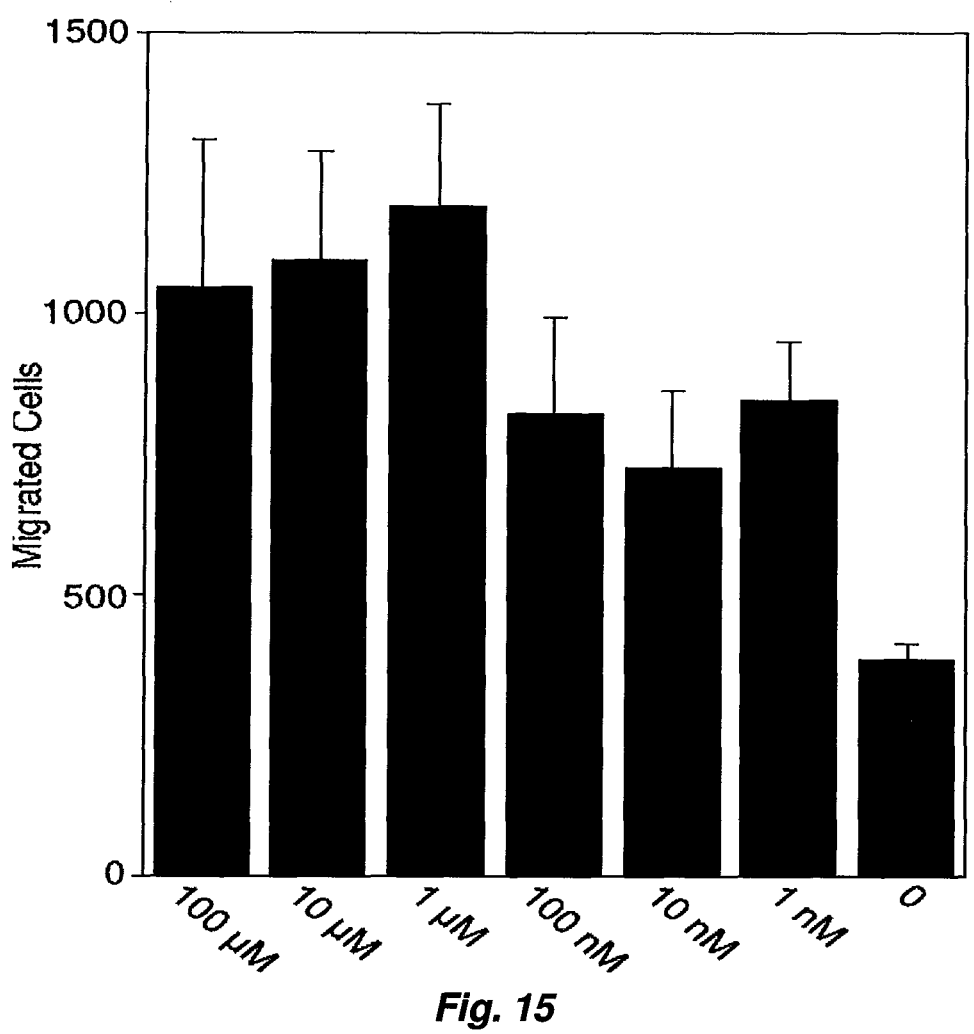
FIG. 15 is a graph showing that Peptide 1 causes migration of human cortical neuroepithelium stem (CTX) cells. The ability of peptide 1 to cause migration of CTX cells was tested over a range of concentrations. Chemotaxis chambers containing $3 \times 10^4$ cells per well were incubated for 5 h and the number of migrated cells counted. Data are means of quadruplicate determinations with SD.

CTX Cell Migration: The ability of peptide 1 to cause the migration of CTX cells was tested (FIG. 15). All concentrations of peptide causes increased migration of CTX cells compared to media without peptide. CTX cell migration was highest at 1 μM peptide.

Implications

Addition of the peptide can cause migration of stem cells. The porcine peptide is chemotactic cross-species for a variety of human stem cell types, not just the perivascular stem cells previously reported. The peptide can cause the formation of the required tissue, in this case bone, at the wound site. Of note, porcine peptide is active in human and mouse, indicating cross-species conservation of function, even with amino acid substitutions. Although the mouse 12-mer aligned sequence is 100% identical to the porcine sequence porcine (100% identity as shown in FIG. 1A), the human sequence differs from the porcine sequence by two amino acids (83% identity as shown in FIG. 1A).

Having described this invention above, it will be understood to those of ordinary skill in the art that the same can be performed within a wide and equivalent range of conditions, formulations and other parameters without affecting the scope of the invention or any embodiment thereof.

We claim:

1. A method of attracting progenitor cells to a location in a patient, comprising administering to a location in the patient one or more isolated and purified polypeptides that:

consist of or consist essentially of sequence IAG-$R_1$-G$R_2$-EK-$R_3$-GG-$R_4$, where $R_1$ is Ile or Val; $R_2$ is Gly or Ala, $R_3$ is Ser or Ala and $R_4$ is Phe or Tyr (SEQ ID NO: 3), e.g., IAGVGGEKSGGF (SEQ ID NO: 1); the sequence GPVGPSGPPGK (SEQ ID NO: 2); or the sequence GPVGPHGPPGK (SEQ ID NO: 7), or a pharmaceutically acceptable salt of thereof;

consist of or consist essentially of a sequence having 75% or greater identity with IAGVGGEKSGGF (SEQ ID NO: 1); a sequence having greater than 90% identity with GPVGPSGPPGK (SEQ ID NO: 2), or a pharmaceutically acceptable salt of thereof;

consist of or consist essentially one of the sequences IAGVGGEKSGGF (SEQ ID NO: 1) or GPVGPSGPPGK (SEQ ID NO: 2), or a pharmaceutically acceptable salt thereof; or consist of 12-50 amino acids comprising: the sequence IAG-$R_1$-G$R_2$-EK-$R_3$-GG-$R_4$, where $R_1$ is Ile or Val; $R_2$ is Gly or Ala, $R_3$ is Ser or Ala and $R_4$ is Phe or Tyr (SEQ ID NO: 3); a sequence having 75% or greater identity with IAGVGGEKSGGF (SEQ ID NO: 1); a sequence having greater than 90% identity with GPVGPSGPPGK (SEQ ID NO: 2); the sequence IAGVGGEKSGGF (SEQ ID NO: 1); the sequence GPVGPSGPPGK (SEQ ID NO: 2); or the sequence GPVGPHGPPGK (SEQ ID NO: 7), or a pharmaceutically acceptable salt thereof.

2. The method of claim 1, wherein the one or more of the isolated and purified polypeptides:

consist of sequence IAG-$R_1$-G$R_2$-EK-$R_3$-GG-$R_4$, where $R_1$ is Ile or Val; $R_2$ is Gly or Ala, $R_3$ is Ser or Ala and $R_4$ is Phe or Tyr (SEQ ID NO: 3), e.g., IAGVGGEKSGGF (SEQ ID NO: 1); the sequence GPVGPSGPPGK (SEQ ID NO: 2); or the sequence GPVGPHGPPGK (SEQ ID NO: 7), or a pharmaceutically acceptable salt of thereof;

consist of a sequence having 75% or greater identity with IAGVGGEKSGGF (SEQ ID NO: 1); a sequence having greater than 90% identity with GPVGPSGPPGK (SEQ ID NO: 2), or a pharmaceutically acceptable salt of thereof; or consist of one of the sequences IAGVGGEKSGGF (SEQ ID NO: 1) or GPVGPSGPPGK (SEQ ID NO: 2), or a pharmaceutically acceptable salt thereof thereby attracting progenitor cells to the location.

3. The method of claim 1, comprising administering an isolated and purified polypeptide chosen from one or both of IAGVGGEKSGGF (SEQ ID NO: 1), or a pharmaceutically acceptable salt thereof, and GPVGPSGPPGK (SEQ ID NO: 2), or a pharmaceutically acceptable salt thereof to the location in the patient.

4. The method of claim 1, wherein the polypeptide is administered in a concentration of at least 100 pM.

5. The method of claim 4, wherein the polypeptide is administered in a concentration of between about 10 pM and 100 µM.

6. The method of claim 4, wherein the polypeptide is administered in a concentration of between about 10 pM and less than or equal to about 10-50 µM.

7. The method of claim 1, in which the progenitor cells are osteogenic.

8. The method of claim 1, in which the isolated and purified polypeptide consists of 12-50 amino acids comprising: the sequence IAG-$R_1$-G$R_2$-EK-$R_3$-GG-$R_4$, where $R_1$ is Ile or Val; $R_2$ is Gly or Ala, $R_3$ is Ser or Ala and $R_4$ is Phe or Tyr (SEQ ID NO: 3); a sequence having 75% or greater identity with IAGVGGEKSGGF (SEQ ID NO: 1); the sequence IAGVGGEKSGGF (SEQ ID NO: 1); or the sequence GPVGPSGPPGK (SEQ ID NO: 2), or pharmaceutical salts thereof.

9. The method of claim 8, wherein the one or more of the isolated and purified polypeptides:

consist of sequence IAG-$R_1$-G$R_2$-EK-$R_3$-GG-$R_4$, where $R_1$ is Ile or Val; $R_2$ is Gly or Ala, $R_3$ is Ser or Ala and $R_4$ is Phe or Tyr (SEQ ID NO: 3), e.g., IAGVGGEKSGGF (SEQ ID NO: 1); the sequence GPVGPSGPPGK (SEQ ID NO: 2); or the sequence GPVGPHGPPGK (SEQ ID NO: 7), or a pharmaceutically acceptable salt of thereof;

consist of a sequence having 75% or greater identity with IAGVGGEKSGGF (SEQ ID NO: 1); a sequence having greater than 90% identity with GPVGPSGPPGK (SEQ ID NO: 2), or a pharmaceutically acceptable salt of thereof; or consist of one of the sequences IAGVGGEKSGGF (SEQ ID NO: 1) or GPVGPSGPPGK (SEQ ID NO: 2), or a pharmaceutically acceptable salt thereof.

10. The method of claim 9, wherein the polypeptide is administered in a concentration of at least 100 pM.

11. The method of claim 10, wherein the polypeptide is administered in a concentration of between about 10 pM and 100 μM.

12. The method of claim 10, wherein the polypeptide is administered in a concentration of between about 10 pM and less than or equal to about 10-50 μM.

13. The method of claim 1, in which the one or more isolated and purified polypeptides are administered at or adjacent to a bone injury or defect.

14. The method of claim 1, in which the one or more isolated and purified polypeptides are administered in a biological scaffold.

15. The method of claim 1, in which the one or more isolated and purified polypeptides are administered by a transdermal device.

* * * * *